United States Patent
Yoon et al.

(10) Patent No.: US 11,222,713 B2
(45) Date of Patent: Jan. 11, 2022

(54) METHODS FOR PREPARING OLIGONUCLEOTIDES FOR DETECTING TARGET NUCLEIC ACID MOLECULES IN SAMPLES

(71) Applicant: SEEGENE, INC., Seoul (KR)

(72) Inventors: Gi-Seok Yoon, Seoul (KR); Jun-Seo Lee, Seoul (KR); Kwang-Il Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 341 days.

(21) Appl. No.: 16/337,970

(22) PCT Filed: Sep. 29, 2017

(86) PCT No.: PCT/KR2017/011039
§ 371 (c)(1),
(2) Date: Mar. 29, 2019

(87) PCT Pub. No.: WO2018/066950
PCT Pub. Date: Apr. 12, 2018

(65) Prior Publication Data
US 2019/0284607 A1   Sep. 19, 2019

(30) Foreign Application Priority Data
Oct. 6, 2016  (KR) ........................ 10-2016-0129326

(51) Int. Cl.
| | | |
|---|---|---|
| *C12Q 1/6806* | (2018.01) | |
| *C12Q 1/6895* | (2018.01) | |
| *G16B 25/00* | (2019.01) | |
| *G16B 25/20* | (2019.01) | |
| *C12Q 1/6876* | (2018.01) | |

(52) U.S. Cl.
CPC ........... *G16B 25/20* (2019.02); *C12Q 1/6806* (2013.01); *C12Q 1/6895* (2013.01); *G16B 25/00* (2019.02); *C12Q 1/6876* (2013.01)

(58) Field of Classification Search
CPC .. C12Q 1/6806; C12Q 1/6876; C12Q 1/6895; C12Q 2525/161; C12Q 2565/514; G16B 25/00; G16B 25/20
See application file for complete search history.

(56) References Cited

U.S. PATENT DOCUMENTS

| | | | |
|---|---|---|---|
| 2006/0204996 A1 | 9/2006 | Kwon et al. | |
| 2007/0259337 A1* | 11/2007 | Hully ..................... | C12Q 1/701 435/5 |
| 2009/0198479 A1 | 8/2009 | Bulla, Jr. et al. | |
| 2014/0080728 A1* | 3/2014 | Nelson ................... | C07H 21/00 506/9 |

FOREIGN PATENT DOCUMENTS

| | | |
|---|---|---|
| KR | 10-2012-0105811 A | 9/2012 |
| WO | WO-2012/096430 A1 | 7/2012 |

OTHER PUBLICATIONS

Matthew C. Thomas et al: "spyder, a new method for in silico design and assessment of 16S rRNA gene primers for molecular microbial ecology: A tool to design and asses 16S rRNA gene primers", FEMS Microbiology Letters, vol. 320, No. 2, May 25, 2011 (May 25, 2011).
Ruslan Kalendar et al: "FastPCR Software for PCR Primer and Probe Design and Repeat Search", Genes, Genomes and Genomics, vol. 3, No. Special Issue 1, Jan. 1, 2009 (Jan. 1, 2009).
Nielsen HB et al., Nucleic Acids Res 31:3491-3496(2003).
Rouillard JM et al., Nucleic Acids Res 31:3057-3062(2003).
Wang X, et al., Bioinformatics 19:796-802(2003).
Hu G, et al., BMC Bioinformatics 8:350(2007).
Wang, D et al., Proc. Natl Acad. Sci. USA, 99:15687-15692(2002).
Lin, F.M et al., IEEE Trans. Inf. Technol. Biomed., 10:705-713(2006).
Chou, C. C et al., BMC Bioinform., 7:232(2006).
Chizhikov, V et al., J. Clin. Microbiol., 40:2398-2407(2002)).
Laassri, M et al., J. Virol. Methods, 112:67-78(2003).
Mehlmann, M. et al, J. Clin. Microbiol., 44:2857-2862(2006).
Extended European Search Report from corresponding European Patent Application No. 17858744.0, dated May 12, 2020.
Hysom, David A. et al., 'Skip the alignment: degenerate, multiplex primer and probe design using K-mer matching instead of alignments', PLoS One, 2012, vol. 7, Issue 4, Article No. e34560 (internal pp. 1-12).
Kutyavin, Igor V., 'Use of base modifications in primers and amplicons to improve nucleic acids detection in the realtime snake polymerase chain reaction', Assay and Drug Development Technologies, 2011, vol. 9, No. 1, pp. 58-68.
Written Opinion of the International Searching Authority from corresponding PCT Application No. PCT/KR2017/011039, dated Dec. 28, 2017.
International Search Report from corresponding PCT/KR2017/011039, dated Dec. 28, 2017.

* cited by examiner

*Primary Examiner* — David C Thomas
(74) *Attorney, Agent, or Firm* — Harness, Dickey & Pierce, P.L.C.

(57) ABSTRACT

The present invention relates to technology for preparing oligonucleotides for detecting a target nucleic acid molecule in a sample. Unlike the conventional methods, the present invention provides a first oligonucleotide candidate group designed appropriately for the first selected nucleotide sequence of the target nucleic acid molecule as a standard instead of simultaneously referring to all of the sequences exhibiting the genetic diversity. Then, an optimal oligonucleotide capable of accurately detecting a target nucleic acid molecule exhibiting genetic diversity in a sample is provided by using the first oligonucleotide candidate group.

19 Claims, 6 Drawing Sheets
Specification includes a Sequence Listing.

METHODS FOR PREPARING OLIGONUCLEOTIDES FOR DETECTING TARGET NUCLEIC ACID MOLECULES IN SAMPLES

CROSS-REFERENCE TO RELATED APPLICATIONS

This application is a national phase application of PCT Application No. PCT/KR2017/011039, filed on Sep. 29, 2017, which claims the benefit and priority to Korean Patent Application No. 10-2016-0129326, filed on Oct. 6, 2016. The entire disclosures of the applications identified in this paragraph are incorporated herein by references.

BACKGROUND OF THE INVENTION

Field of the Invention

The present invention relates to technology for preparing oligonucleotides for detecting a target nucleic acid molecule in a sample.

Description of the Related Art

There have been known many methods for the detection of a target nucleic acid molecule in the art. Examples of the various detection methods include PTOCE (PTO cleavage and extension) method (WO 2012/096523), TaqMan probe method (U.S. Pat. No. 5,210,015), Molecular beacon method (Tyagi et al., Nature Biotechnology 14:303(1996)), Scorpion method (Whitcombe et al., Nature Biotechnology 17:804-807(1999)), Sunrise or Amplifluor method (Nazarenko et al., 2516-2521 Nucleic Acids Research, 25(12): 2516(1997), and U.S. Pat. No. 6,117,635), Lux method (U.S. Pat. No. 7,537,886), CPT (Duck P, et al., Biotechniques, 9:142-148(1990)), LNA method (U.S. Pat. No. 6,977,295), Plexor method (Sherrill C B et al., Journal of the American Chemical Society, 126:4550-4556(2004)), Hybeacons method (D. J. French, et al., Molecular and Cellular Probes (2001) 13, 363-374 and U.S. Pat. No. 7,348,141), Dual-labeled self-quenched probes (U.S. Pat. No. 5,876,930), Hybridization probes (Bernard P S, et al., Clin Chem 2000, 46, 147-148), Invader assay (U.S. Pat. No. 5,691,142), PCE-SH (PTO Cleavage and Extension-Dependent Signaling Oligonucleotide Hybridization) method (WO 2013/115442), PCE-NH (PTO Cleavage and Extension-Dependent Non-Hybridization) method (WO 2014/104818) and CER method (WO 2011/037306).

For detection of a target nucleic acid molecule, oligonucleotides (probes and/or primers) used have to have suitable specificity and sensitivity and be suitable for a particular detection process and compatible with conditions set by an analyst. Therefore, the design of oligonucleotides suitable for an analysis purpose is very important.

A number of techniques have been proposed for the design of oligonucleotides (Nielsen H B et al., Nucleic Acids Res 31:3491-3496(2003); Rouillard J M et al., *Nucleic Acids Res* 31:3057-3062(2003); Wang X, et al., *Bioinformatics* 19:796-802(2003); and Hu G, et al., *BMC Bioinformatics* 8:350(2007)).

The design of oligonucleotides becomes more difficult when target nucleic acid molecules (particularly, genomic sequences of RNA viruses) have sequence variability (genetic diversity). In order to detect target nucleic acid molecules having genetic diversity with a suitable coverage, a more sophisticated oligonucleotide design is required and in the case of multiplex detection, the difficulty of designing such an oligonucleotide becomes more remarkable.

There have been various attempts to design oligonucleotides for detecting target nucleic acid molecules with genetic diversity. A common method of designing such oligonucleotides is to find a conserved region from multiple target nucleic acid molecules with genetic diversity and to design oligonucleotides that hybridize with this region (see, Wang, D et al., *Proc. Natl Acad. Sci. USA*, 99:15687-15692 (2002); Lin, F. M et al., *IEEE Trans. Inf. Technol. Biomed.*, 10:705-713(2006); Chou, C. C et al., *BMC Bioinform.*, 7:232(2006); Chizhikov, V et al., *J. Clin. Microbiol.*, 40:2398-2407(2002)); Laassri, M et al., *J. Virol. Methods*, 112:67-78(2003) Mehlmann, M. et al, *J. Clin. Microbiol.*, 44:2857-2862(2006)).

Conventional oligonucleotide design methods using conserved regions found by a pairwise sequence comparison or multiple sequence comparison have shortcomings in light of the fact that their computational processing becomes increasingly difficult in parallel with accumulation of huge sequence information.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop a method capable of efficiently providing oligonucleotides (e.g., primers and probes) to detect a target nucleic acid molecule, particularly a target nucleic acid molecule exhibiting genetic diversity. A number of sequences showing genetic diversity are being newly identified after probes and/or primers for detecting a target nucleic acid molecule have been already proposed, leading to increase in a target nucleic acid sequence pool to be detected for diagnosis. For accommodating such situation, we have intensively studied to develop a method capable of providing probes and/or primers to more easily detect an increased target nucleic acid sequence pool. As a result, we have developed a unique method for providing oligonucleotides, which is distinctly different from the conventional methods. Instead of simultaneously referring to all of sequences exhibiting genetic diversity as conventional methods, the present invention provides a first oligonucleotide candidate group designed for a first selected nucleotide sequence of a target nucleic acid molecule as a standard, and then provides most workable oligonucleotides by using the first oligonucleotide candidate group, which are able to accurately detect a target nucleic acid molecule exhibiting genetic diversity in a sample.

Accordingly, it is an object of this invention to provide a method for preparing oligonucleotides for detecting a target nucleic acid molecule in a sample.

It is another object of this invention to provide a computer readable storage medium containing instructions to configure a processor to perform a method for preparing oligonucleotides for detecting a target nucleic acid molecule in a sample.

It is still another object of this invention to provide a computer readable storage medium containing instructions to configure a processor to perform a method for preparing oligonucleotides for detecting a target nucleic acid molecule in a sample.

It is further object of this invention to provide a device for preparing oligonucleotides for detecting of a target nucleic acid molecule in a sample.

Other objects and advantages of the present invention will become apparent from the detailed description to follow taken in conjugation with the appended claims and drawings.

DETAILED DESCRIPTION OF THIS INVENTION

Figure 1:
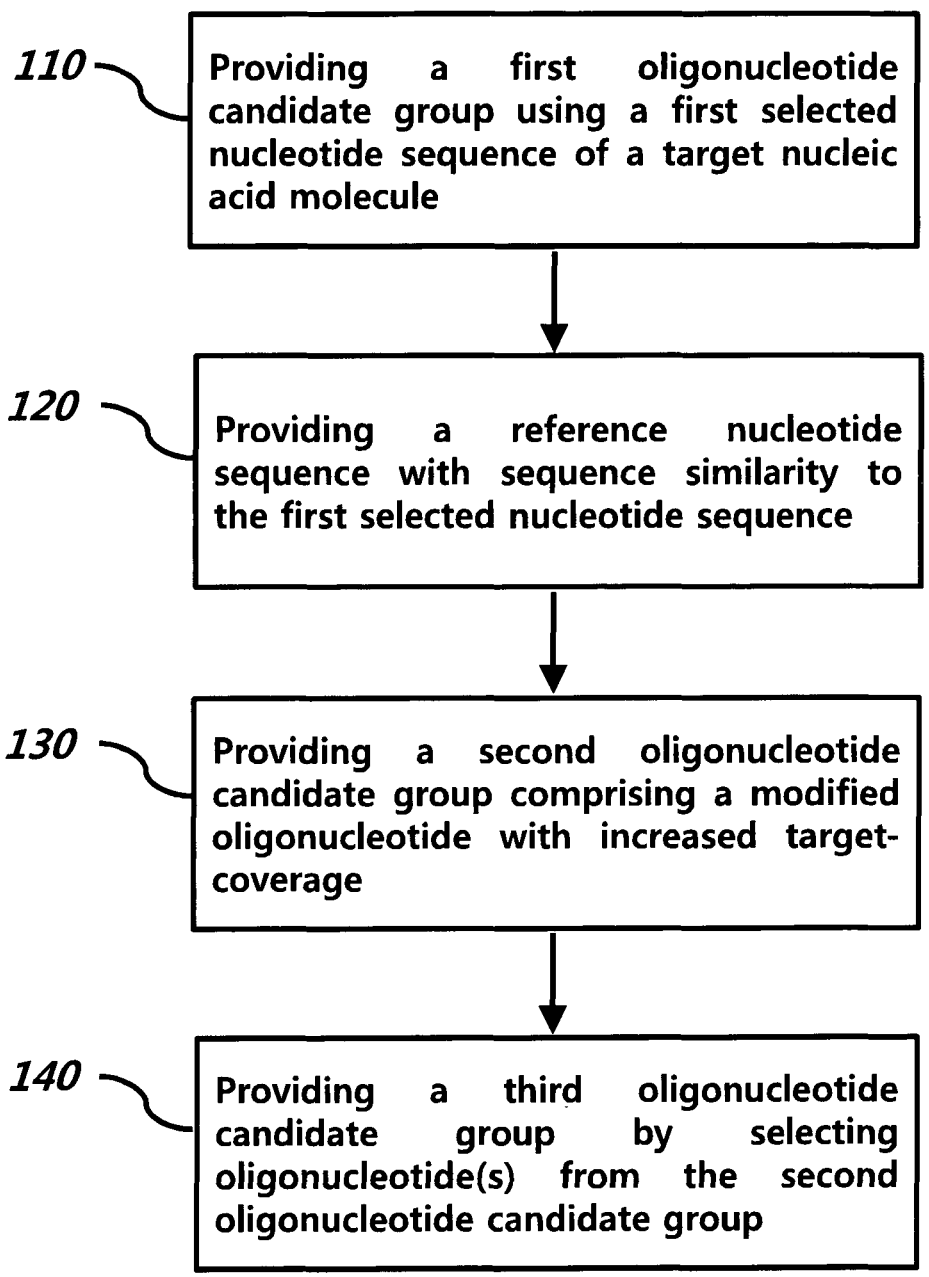
FIG. 1 is a flow diagram representing an embodiment of the present method for preparing oligonucleotides for detecting a target nucleic acid molecule in a sample.
Figure 2:
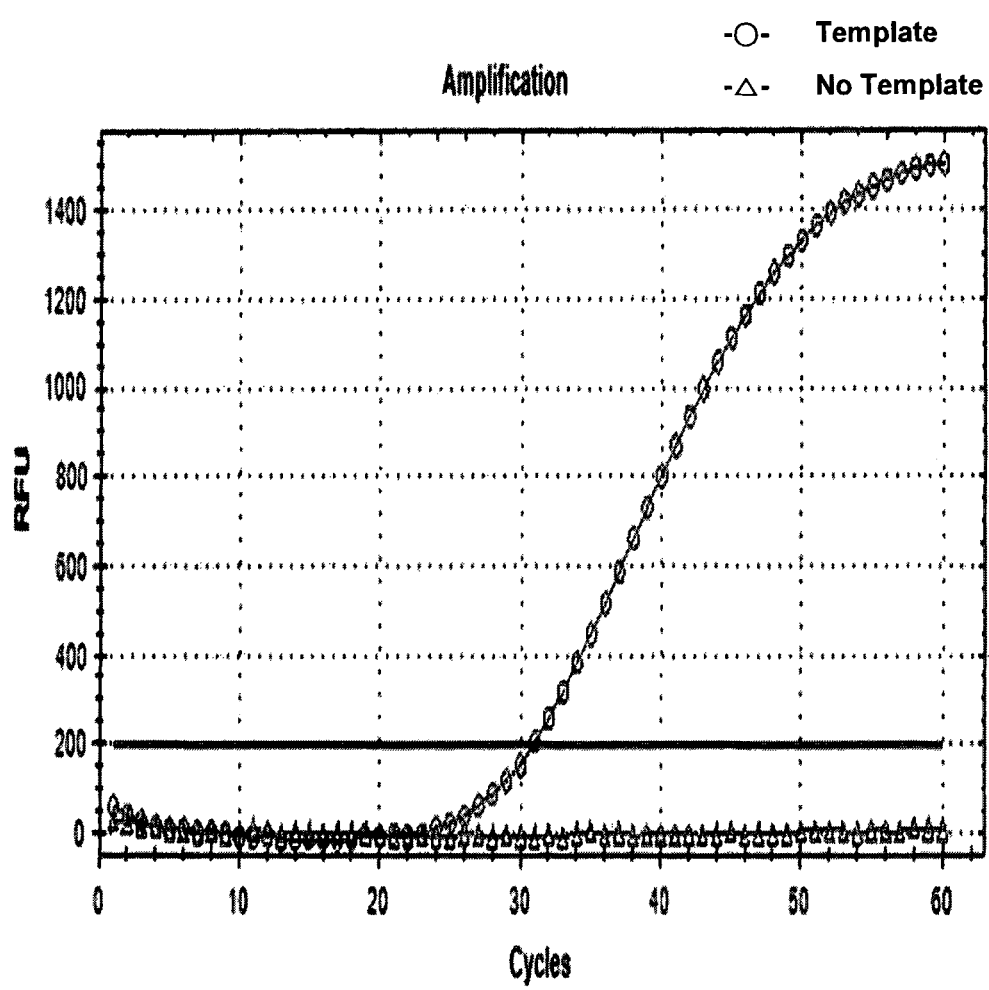
FIG. 2 shows the results of the real-time detection of Candida albicans (tax_id: 5476) gene by the PTOCE assay (see WO 2012/096523) using probes and primers prepared by the present method.
Figure 3:
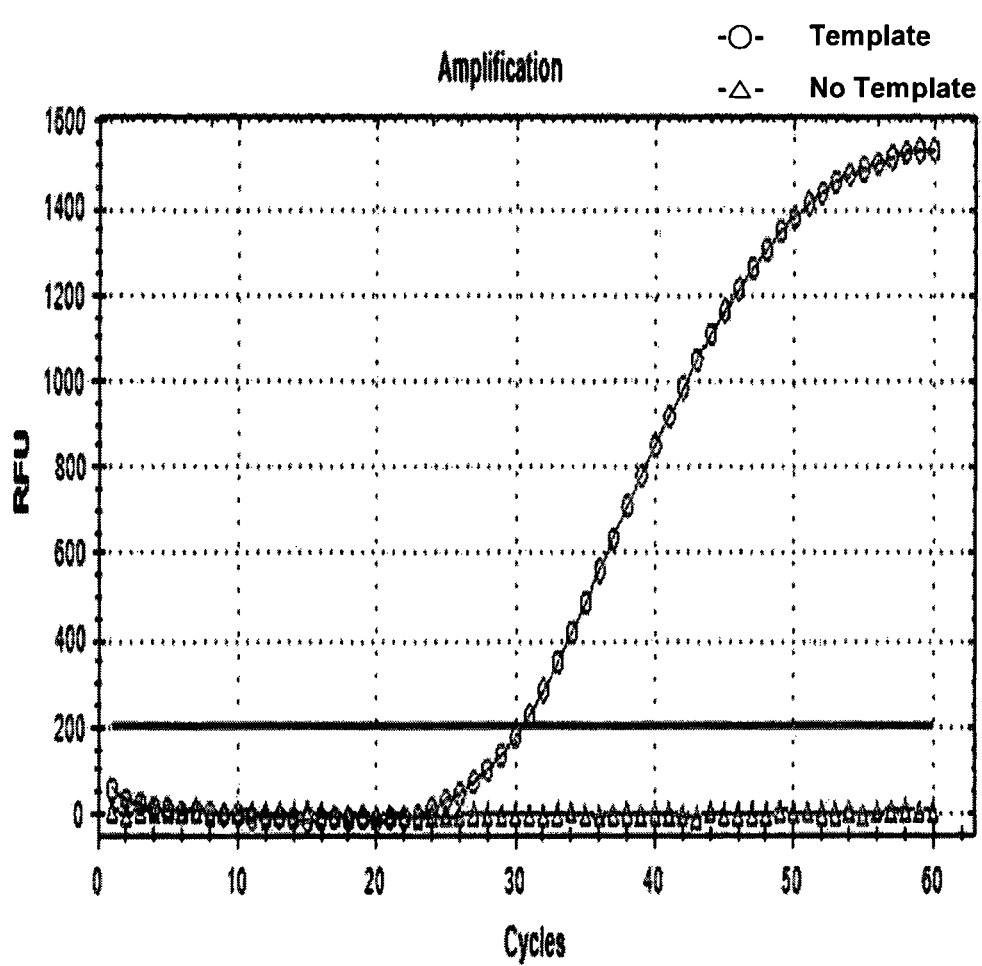
FIG. 3 shows the results of the real-time detection of Candida albicans WO-1 (tax_id: 294748) gene by PTOCE assay using probes and primers prepared by the present method.
Figure 4:
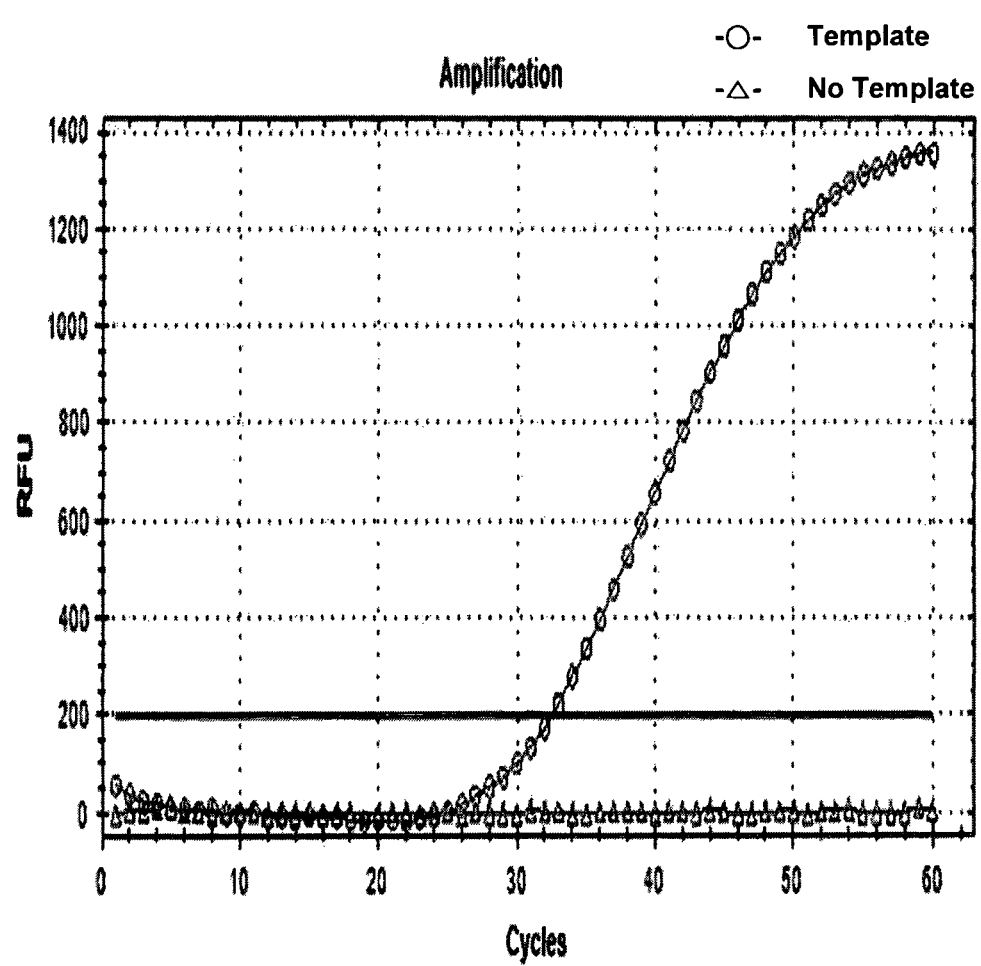
FIG. 4 represents the results of the real-time detection of Candida albicans A203 (tax_id: 1182540) gene by PTOCE assay using probes and primers prepared by the present method.
Figure 5:
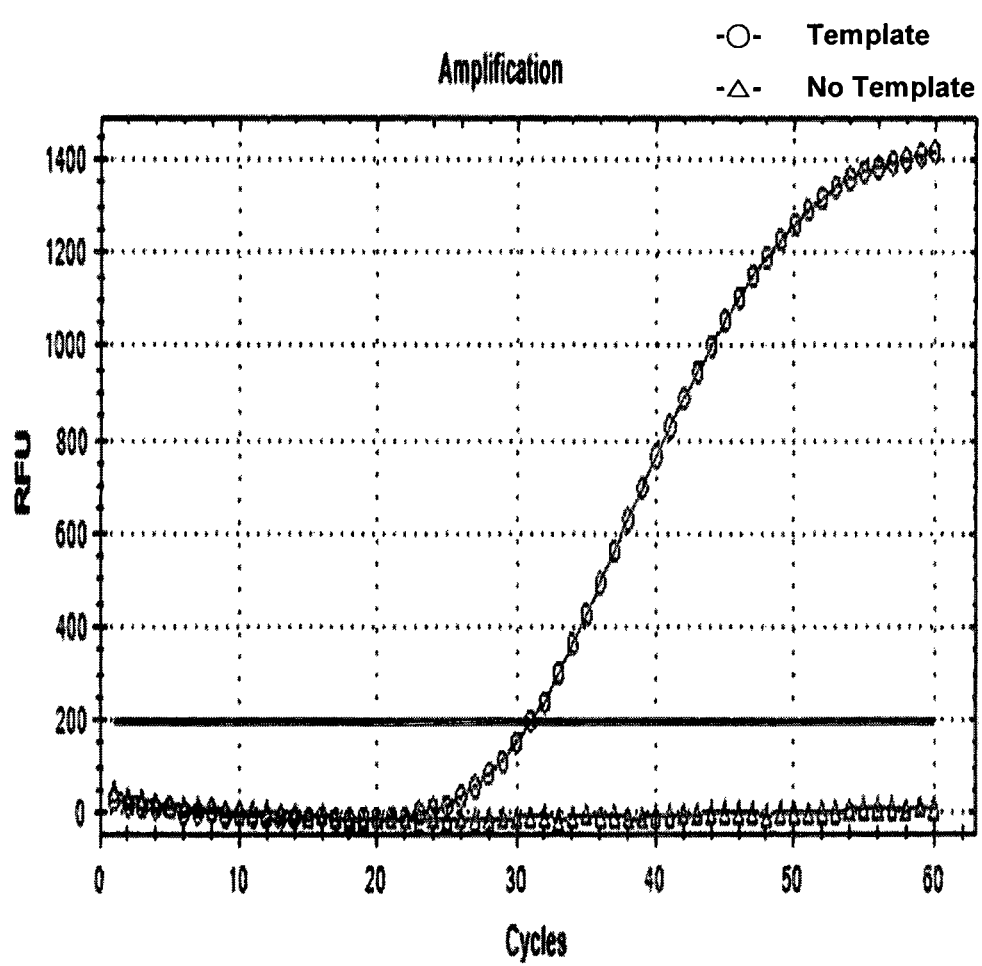
FIG. 5 represents the results of the real-time detection of Candida albicans 12C (tax_id: 1094981) gene by PTOCE assay using probes and primers prepared by the present method.
Figure 6:
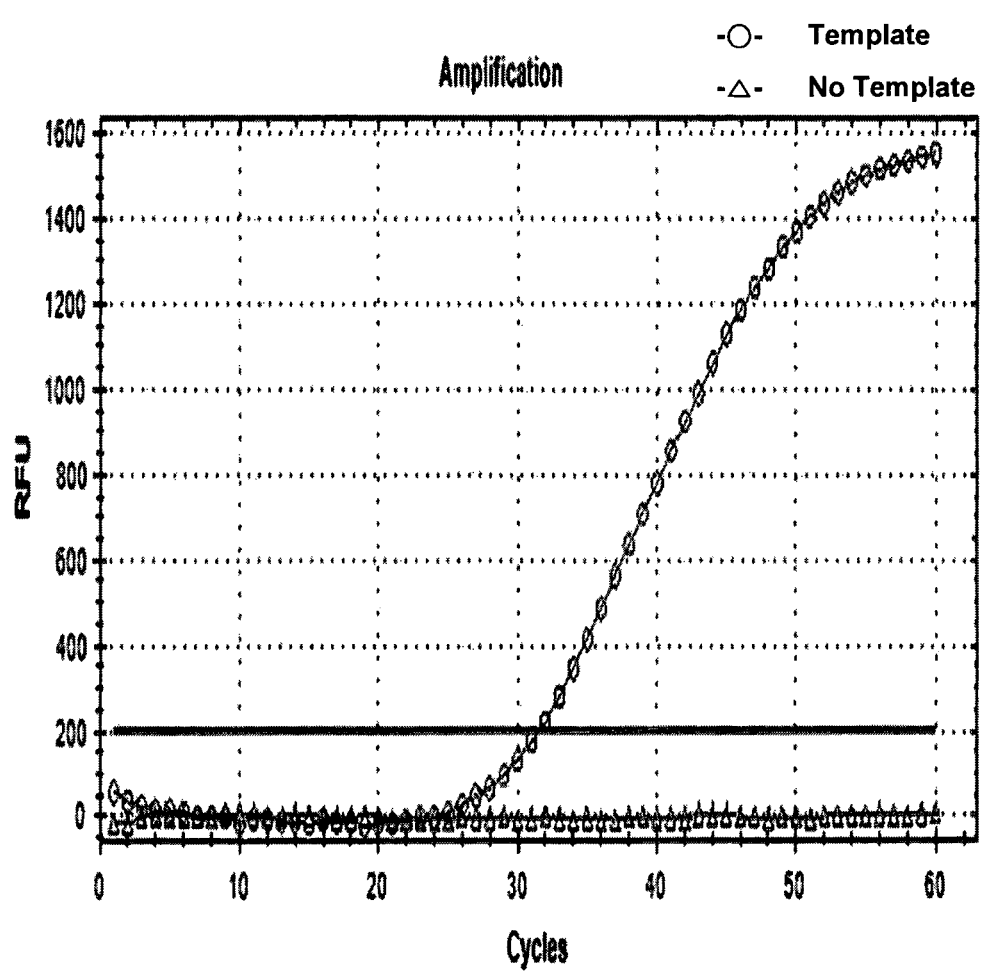
FIG. 6 shows the results of the real-time detection of Candida albicans 3153A (tax_id: 1182531) gene by PTOCE assay using probes and primers prepared by the present method.

I. Method for Preparing Oligonucleotides for Detecting a Target Nucleic Acid Molecule in a Sample In one aspect of the present invention, there is provided a method for preparing oligonucleotides for detecting a target nucleic acid molecule in a sample, comprising:

designing oligonucleotides for detecting the target nucleic acid molecule in the sample using information related to the target nucleic acid molecule to provide a first oligonucleotide candidate group; wherein the information related to the target nucleic acid molecule comprises a first selected nucleotide sequence of the target nucleic acid molecule and the first oligonucleotide candidate group comprises a probe and/or a primer comprising a nucleotide sequence complementary to the first selected nucleotide sequence of the target nucleic acid molecule;

providing at least one reference nucleotide sequence with sequence similarity to the first selected nucleotide sequence of the target nucleic acid molecule;

providing a second oligonucleotide candidate group using the first oligonucleotide candidate group; wherein the provision is performed by at least one of the followings;

(a-1) in the first oligonucleotide candidate group, selecting at least one oligonucleotide showing a predetermined target-coverage for the first selected nucleotide sequence and the at least one reference nucleotide sequence to provide a second oligonucleotide candidate group comprising the at least one oligonucleotide; and (a-2) in the first oligonucleotide candidate group, replacing with a degenerate base and/or a universal base at least one base of at least one oligonucleotide showing a target-coverage of less than 100% for the first selected nucleotide sequence and at least one reference nucleotide sequence to provide a modified oligonucleotide with increased target-coverage, thereby providing the second oligonucleotide candidate group comprising the modified oligonucleotide; and selecting oligonucleotide(s) depending on a predetermined selection criterion from the second oligonucleotide candidate group to provide a third oligonucleotide candidate group; wherein the third oligonucleotide candidate group is used for detecting the target nucleic acid molecule in the sample.

The present inventors have made intensive researches to develop a method capable of efficiently providing oligonucleotides (e.g., primers and probes) to detect a target nucleic acid molecule, particularly a target nucleic acid molecule exhibiting genetic diversity. A number of sequences showing genetic diversity are being newly identified after probes and/or primers for detecting a target nucleic acid molecule have been already proposed, leading to increase in a target nucleic acid sequence pool to be detected for diagnosis. For accommodating such situation, we have intensively studied to develop a method capable of providing probes and/or primers to more easily detect an increased target nucleic acid sequence pool. As a result, we have developed a unique method for providing oligonucleotides, which is distinctly different from the conventional methods. Instead of simultaneously referring to all of sequences exhibiting genetic diversity as conventional methods, the present invention provides a first oligonucleotide candidate group designed for a first selected nucleotide sequence of a target nucleic acid molecule as a standard and then provides most workable oligonucleotides by using the first oligonucleotide candidate group, which are able to accurately detect a target nucleic acid molecule exhibiting genetic diversity in a sample.

FIG. 1 is a flow diagram representing an embodiment of the present method for preparing oligonucleotides for detecting a target nucleic acid molecule in a sample. The method of the present invention will be described with reference to FIG. 1 as follows:

Step: Providing a First Oligonucleotide Candidate Group (110)

The oligonucleotides for detecting the target nucleic acid molecule in the sample using information related to the target nucleic acid molecule are designed to provide a first oligonucleotide candidate group. The information related to the target nucleic acid molecule comprises a first selected nucleotide sequence of the target nucleic acid molecule and the first oligonucleotide candidate group comprises a probe and/or a primer comprising a nucleotide sequence complementary to the first selected nucleotide sequence of the target nucleic acid molecule.

The oligonucleotides for detecting the target nucleic acid molecule are designed using information related to the target nucleic acid molecule and the information related to the target nucleic acid molecule comprises the first selected nucleotide sequence of the target nucleic acid molecule.

The term used herein "target nucleic acid molecule" refers to a nucleic acid molecule to be detected by an experimenter. The target nucleic acid molecule is not required to have any certain sequence or length, and the target nucleic acid molecule includes all DNA (gDNA and cDNA) and RNA molecules. The target nucleic acid sequence may be in a double strand or single strand.

The target nucleic acid molecule includes all natural prokaryotic cell nucleic acid, eukaryotic cell (e.g., protozoan and parasitic animal, fungus, yeast, higher plant, lower animal and higher animal including mammal and human) nucleic acid, virus (e.g., herpes virus, Adenovirus, HBV, HIV, HPV, influenza virus, Epstein-Barr virus, hepatitis virus, poliovirus, etc.) nucleic acid or viroid nucleic acid.

Particularly, when the target nucleic acid molecule exhibits sequence variability (i.e., genetic diversity), the term "target nucleic acid molecule" refers to a nucleic acid molecule that may be represented by a variety of sequences including various genetic variations. For example, in the case of detecting the L1 gene of HPV type 16 showing genetic diversity, the L1 gene is the target nucleic acid molecule and an exact sequence of the L1 gene of HPV type 16 in the sample to be actually detected, which includes various L1 gene sequences, is not recognized before analysis such as sequencing and PCR.

According to an embodiment of the present invention, the target nucleic acid molecule is a nucleic acid molecule that exhibits genetic diversity. The genetic diversity has been reported in various genomes. Particularly, the genetic diversity is most frequently found and occurs in viral genomes (Nathalie B. et al., Journal of Clinical Microbiology, 42:3532(2004); Tersa C. et al., Journal of Infectious Diseases, 185:1660(2002); Takashi E. et al., Journal of Clinical Microbiology, 42:126(2004); and Elizabeth R. et al. Clinical Infectious Diseases, 32:1227(2001)).

The term used herein "target nucleic acid molecule in a sample" refers to a target nucleic acid molecule having a certain sequence actually contained in a sample to be analyzed.

The term used herein, "sample" comprises biological samples (e.g., cells, tissues and body fluids) and non-biological samples (e.g., food, water and soil), and the biological samples may include, for example, virus, bacteria, tissue, cell, blood (including whole blood, plasma and serum), lymph, bone marrow, saliva, sputum, swab, aspiration, milk, urine, feces, ocular fluid, semen, brain extract, spinal fluid, joint fluid, thymus fluid, bronchial washing fluid, ascites and amniotic fluid. The sample may be subjected to a nucleic acid extraction procedure known in the art (see, Sambrook, J. et al., *Molecular Cloning, A Laboratory Manual,* 3rd ed. Cold Spring Harbor Press (2001). The nucleic acid extraction process may vary depending on the kind of the sample. In addition, when the extracted nucleic acid is RNA, a reverse transcription process for synthesizing cDNA may be further performed (see, Sambrook, J. et al., *Molecular Cloning, A Laboratory Manual,* 3rd ed., Cold Spring Harbor Press (2001).

The oligonucleotides for detecting target nucleic acid molecules in a sample are designed by using (for example, by considering) the first selected nucleotide sequence as information related to the target nucleic acid molecule.

The term used herein "a first selected nucleotide sequence" refers to a selected nucleotide sequence of a target nucleic acid molecule as a standard for providing a first oligonucleotide candidate group. For example, when the target nucleic acid molecule exhibits genetic diversity, the term "a first selected nucleotide sequence" refers to a sequence selected from various sequences representing a target nucleic acid molecule.

For example, the first selected nucleotide sequence may comprise a sequence provided by an experimenter to an oligonucleotide manufacturer, a sequence searched by the oligonucleotide manufacturer based on the sequence name information (e.g., gene name) presented by an experimenter and a sequence provided in such a manner that an oligonucleotide manufacturer selects a gene based on a target organism name information presented by an experimenter and then searches for its sequence.

According to an embodiment of the present invention, the information related to the target nucleic acid molecule used to design the oligonucleotides additionally comprises at least one information selected from the group consisting of a name of a target organism from which the target nucleic acid molecule is derived, a taxonomy of a target organism, a name of the target nucleic acid molecule and an identifier of the target nucleic acid molecule in a public accessible sequence database. The additional information may be used as information for obtaining the first selection nucleotide sequence of the target nucleic acid molecule.

For example, an oligonucleotide orderer may notify a manufacturer of only a target organism name (e.g., HPV type 16) to be detected rather than sequence information. In this case, the oligonucleotide manufacturer may design oligonucleotides by selecting a gene and its sequence suitable for detection of the target organism. Alternatively, an oligonucleotide orderer may only inform a manufacturer of a target nucleic acid molecule name (e.g., L1 gene of HPV type 16). In this case, the oligonucleotide manufacturer may design oligonucleotides by selecting a sequence of the L1 gene of HPV type 16. In addition, an oligonucleotide orderer may notify a manufacturer of only an identifier of a target nucleic acid molecule in a publicly accessible sequence database. The identifier includes, for example, an accession number, a locus name, and a gi number in GenBank DB, and particularly, an access number. In this case, the oligonucleotide manufacturer may obtain sequence information of the target nucleic acid molecule in the database based on the identifier and then design oligonucleotides based on the sequence information.

More particularly, the information related to the target nucleic acid molecule used to design the oligonucleotides is the first selected nucleotide sequence of the target nucleic acid molecule and the name of a target organism from which the target nucleic acid molecule is derived.

The length of the first selected nucleotide sequence used to provide a first oligonucleotide candidate group is not particularly limited, and may have a total length or a partial length of the target nucleic acid molecule, and for example, have a length of 300-10,000 nucleotides. The first selection nucleotide sequence may be a gDNA sequence, mRNA sequence or cDNA sequence of the target nucleic acid molecule.

To provide a first oligonucleotide candidate group, at least two oligonucleotides (i.e., probe and/or primer) comprising a sequence complementary to the first selected nucleotide sequence of the target nucleic acid molecule are designed.

Particularly, the first oligonucleotide candidate group is provided by designing at least 10, at least 20, at least 30, at least 40, at least 50, at least 60, at least 70, at least 80, at least 90 or at least 100 oligonucleotides complementary to various regions of the first selected nucleotide sequence of the target nucleic acid molecule. Particularly, the first oligonucleotide candidate group is a pool of probes and/or primers.

The term "complementary" is used herein to mean that primers or probes are sufficiently complementary to hybridize selectively to a target nucleic acid molecule under the designated annealing conditions or stringent conditions, encompassing the terms "substantially complementary" and "perfectly complementary", preferably perfectly complementary.

The first oligonucleotide candidate group includes primers and/or probes used in various detection methods. Examples of the various detection methods include PTOCE (PTO cleavage and extension) method (WO 2012/096523), TaqMan probe method (U.S. Pat. No. 5,210,015), Molecular beacon method (Tyagi et al., Nature Biotechnology 14:303 (1996)), Scorpion method (Whitcombe et al., Nature Biotechnology 17:804-807(1999)), Sunrise or Amplifluor method (Nazarenko et al., 2516-2521 Nucleic Acids Research, 25(12):2516(1997), and U.S. Pat. No. 6,117,635), Lux method (U.S. Pat. No. 7,537,886), CPT (Duck P, et al., Biotechniques, 9:142-148(1990)), LNA method (U.S. Pat. No. 6,977,295), Plexor method (Sherrill C B et al., Journal of the American Chemical Society, 126:4550-4556(2004)), Hybeacons method (D. J. French, et al., Molecular and Cellular Probes (2001) 13, 363-374 and U.S. Pat. No. 7,348,141), Dual-labeled self-quenched probes (U.S. Pat. No. 5,876,930), Hybridization probes (Bernard P S, et al., *Clin Chem* 2000, 46, 147-148), Invader assay (U.S. Pat. No. 5,691,142), PCE-SH (PTO Cleavage and Extension-Dependent Signaling. Oligonucleotide Hybridization) method (WO 2013/115442), PCE-NH (PTO Cleavage and Extension-Dependent Non-Hybridization) method (WO 2014/104818) and CER method (WO 2011/037306).

According to an embodiment, the first oligonucleotide candidate group comprises a primer and a probe used for detection of the target nucleic acid molecule.

For example, the first oligonucleotide candidate group includes primers and probes used in PTOCE method or TaqMan probe method. For example, the first oligonucleotide candidate group includes a probe [i.e., a probing and tagging oligonucleotide (PTO)] and a primer used in PTOCE method.

According to an embodiment of the present invention, the probe of the first selected oligonucleotide candidate group is a tagging probe comprising a targeting portion comprising a hybridizable-complementary nucleotide sequence to the first selected nucleotide sequence of the target nucleic acid molecule and a tagging portion comprising a non-hybridizable-non-complementary nucleotide sequence to the first selected nucleotide sequence of the target nucleic acid molecule.

A representative example of such a tagging probe is a PTO used in PTOCE method.

The tagging probe may be prepared in various ways.

According to an embodiment, the tagging probe is provided by a method comprising the following steps:

(a) selecting the hybridizable-complementary nucleotide sequence to the first selected nucleotide sequence of the target nucleic acid molecule for the targeting portion and the non-hybridizable-non-complementary nucleotide sequence to the first selected nucleotide sequence of the target nucleic acid molecule for the tagging portion; wherein the tagging portion comprises a first tagging part of 3-8 nucleotides in length adjacent to the targeting portion and a second tagging part of 4-40 nucleotides in length adjacent to the first tagging part; the non-hybridizable-non-complementary nucleotide sequence for the tagging portion is selected not to be hybridized with the first selected nucleotide sequence of the target nucleic acid molecule; wherein a non-hybridizable-non-complementary nucleotide sequence of the first tagging part is selected by an independent non-complementarity level such that a sequence with a non-complementarity level satisfying a predetermined threshold value criterion is selected as the non-hybridizable-non-complementary nucleotide sequence of the first tagging part; and (b) preparing the tagging probe comprising (i) the targeting portion comprising the selected hybridizable-complementary nucleotide sequence and (ii) the tagging portion comprising the selected non-hybridizable-non-complementary nucleotide sequence.

The length of the first tagging part may be, for example, 2-8 nucleotides, 2-7 nucleotides, 2-6 nucleotides, 2-5 nucleotides, 2-4 nucleotides, 2-8 nucleotides, 2-7 nucleotides, 2-6 nucleotides, 2-5 nucleotides, 3-8 nucleotides, 3-7 nucleotides, 3-6 nucleotides, 3-5 nucleotides, 3-4 nucleotides, 4-8 nucleotides, 4-7 nucleotides, 4-6 nucleotides, or 4-5 nucleotides. The length of the second tagging part may be, for example, 4-40 nucleotides, 4-30 nucleotides, 4-25 nucleotides, 4-20 nucleotides, 4-15 nucleotides, 4-12 nucleotides, 4-10 nucleotides, 4-6 nucleotides, 6-40 nucleotides, 6-30 nucleotides, 6-25 nucleotides, 6-20 nucleotides, 6-15 nucleotides, 6-12 nucleotides, 6-10 nucleotides, 8-40 nucleotides, 8-30 nucleotides, 8-25 nucleotides, 8-20 nucleotides, 8-15 nucleotides, 8-12 nucleotides, or 8-10 nucleotides.

According to the method, the sequence selection of the first tagging part is performed by an independent non-complementarity level for the partial sequence of the tagging portion, i.e., the first tagging part. The term used herein "non-complementarity level" refers to the degree to which the tagging portion or a part of the tagging portion (e.g., the first tagging part) does not form Watson-Crick base pairs with a target nucleic acid sequence. The term "non-complementarity level" may be used interchangeably with the ordinary term "non-complementarity" in the art, but particularly the term "non-complementarity level" means a value obtained from unfavorability between nucleotide bases. According to the present invention, a score may be given in consideration of the binding force for each base pair and used as the unfavorability. Alternatively, a ranking may be given in consideration of the binding force for each base pair, a score may be then given for each ranking or ranking section, and the score may be used as the unfavorability. The non-complementarity level between sequences comprising a plurality of nucleotides may be obtained from the unfavorability of each base pair. The higher the non-complementarity level of a sequence is, the more suitable it is as the sequence of the first tagging part.

Alternatively, the tagging probe is provided by a method comprising the following steps:

(a) providing a nucleotide sequence for the tagging portion; wherein the tagging portion comprises a first tagging part adjacent to the targeting portion and a second tagging part adjacent to the first tagging part;

(b) selecting in the first selected nucleotide sequence of the target nucleic acid molecule one or more non-hybridizable-non-complementary regions to the nucleotide sequence for the tagging portion by (i) selecting at least one region in the first selected nucleotide sequence of the target nucleic acid molecule and (ii) evaluating a non-complementarity level of the selected at least one region to the nucleotide sequence for the tagging portion;

(c) selecting a nucleotide sequence for the targeting portion by (i) selecting a nucleotide sequence with a predetermined length in the first selected nucleotide sequence of the target nucleic acid molecule that is adjacent to the non-hybridizable-non-complementary region to the nucleotide sequence of the tagging portion and (ii) selecting a hybridizable-complementary nucleotide sequence to the selected nucleotide sequence in the first selected nucleotide sequence of the target nucleic acid molecule as the nucleotide sequence for the targeting portion; and (d) preparing the tagging probe comprising the nucleotide sequence of the tagging portion provided in the step (a) and the nucleotide sequence of the targeting portion selected in the step (c).

According to the first method, the hybridizable-complementary nucleotide sequence of the targeting portion is first selected and then as the tagging portion selected is the non-hybridizable-non-complementary nucleotide sequence to a sequence of the target nucleic acid sequence adjacent to a sequence with which the targeting portion is hybridized.

According to the second method, the non-hybridizable-non-complementary nucleotide sequence of the tagging portion is first selected and then as the targeting portion selected is the hybridizable-complementary nucleotide sequence to a sequence of the target nucleic acid sequence adjacent to a sequence opposite to the sequence of the tagging portion. The technical descriptions of the two methods are the same except for the differences described above and therefore the technical descriptions for the first method may apply to the second method.

The probes and/or the primers of the first oligonucleotide candidate group may be designed to comprise all of oligonucleotides having a sequence complementary to the first selected nucleotide sequence of the target nucleic acid molecule.

Alternatively, the probes and/or the primers of the first oligonucleotide candidate group may be designed to comprise an oligonucleotide which has a sequence complementary to the first selected nucleotide sequence of the target nucleic acid molecule and satisfies certain criteria.

According to an embodiment of the present invention, the designed first oligonucleotide candidate group comprises a probe designed to satisfy at least one of the following criteria: (i) a $T_m$ value of 50° C. to 85° C.; (ii) a length of 15-50 nucleotides; (iii) exclusion of a mononucleotide $(G)_n$ run sequence in which n is at least 3; (iv) GC content of the 5'-end portion of 40% or more; (v) for the tagging probe, the targeting portion of which 5'-end is G or C; and (vi) for the tagging probe, the targeting portion of which 5'-end portion has GC content of 40% or more.

More particularly, the probe design criteria include at least two of the above criteria, more particularly at least three, more particularly at least four, and more particularly, five criteria.

The $T_m$ value of the design criteria is, for example, 50°-80° C., 50-75° C., 55-80° C.; 55-75° C., 60-80° C., 60-75° C., 65-80° C. or 60-75° C. Particularly, the $T_m$ value of the design criteria is 55-80° C., 60-78° C., 63-78° C., 65-75° C., 67-75° C. or 65-73° C. Where the probe is a tagging probe, the description of the $T_m$ value is applied to the targeting region of the tagging probe.

The length of the design criteria may be, for example, 10-60 nucleotides, 10-50 nucleotides, 10-45 nucleotides, 10-40 nucleotides or 10-35 nucleotides, 15-60 nucleotides, 15-50 nucleotides, 15-45 nucleotides, 15-40 nucleotides or 15-35 nucleotides. Where the probe is a tagging probe, the description of the length is applied to the targeting site of the tagging probe.

Among the design criteria, a mononucleotide $(G)_n$ run sequence in which for example, n is at least 3 or 4 is excluded.

According to an embodiment of the present invention, the designed first oligonucleotide candidate group comprises a tagging probe designed to satisfy at least one of the following criteria: (i) a $T_m$ value of 50° C. to 85° C. of the targeting portion; (ii) a length of 15-50 nucleotides of the targeting portion; (iii) exclusion of a mononucleotide $(G)_n$ run sequence in which n is at least 3 of the targeting portion; (iv) the targeting portion of which 5'-end is G or C; (v) the targeting portion of which 5'-end portion has GC content of 40% or more; (vi) a length of 6-30 nucleotides of the tagging portion; (vii) inclusion of at least 30% of the mismatch sequence based on the length of the tagging portion, and (viii) inclusion of at least 40% of the mismatch sequence based on the length of the 3'-end part of the tagging portion.

Among the design criteria for the targeting portion of the tagging probe, $T_m$ value, length, and G-run sequence exclusion may be described with reference to the description of the general probe.

For the tagging probe, the targeting portion of which 5'-end portion has GC content of 40% or more, particularly, 40-70% or 40-60%. The 5'-end portion means a portion within 10 nucleotides from the 5'-end of the targeting portion.

The length of the tagging portion is particularly 6-20 nucleotides, 10-30 nucleotides, 10-20 nucleotides, 12-30 nucleotides or 12-20 nucleotides.

The tagging portion has to be sufficiently non-complementary to a certain region of a nucleic acid sequence such that it is not hybridized with the certain region under conditions in which the targeting portion of the tagging probe is hybridized with the certain region. Particularly, the tagging portion includes 40% or more, more particularly 50% or more of the mismatch sequence based on its length. Particularly, the 3'-end portion of the tagging region comprises 50% or more of the mismatch sequence based on its length.

According to an embodiment of the present invention, the designed first oligonucleotide candidate group comprises a primer designed to satisfy at least one of the following criteria: (i) a $T_m$ value of 40° C. to 70° C.; (ii) a length of 15-60 nucleotides; and (iii) exclusion of a mononucleotide $(G)_n$ run sequence in which n is at least 3.

The $T_m$ value of the design criteria is, for example, 40-70° C., 50-70° C., 55-70° C., 45-65° C., 50-65° C., 55-65° C., 45-60° C., or 50-65° C. Particularly, the $T_m$ value of the design criteria is 40-70° C., 45-65° C., 50-65° C., 50-60° C., 55-65° C., or 55-60° C.

The length of the design criteria may be, for example, 15-60 nucleotides, 15-50 nucleotides, 15-45 nucleotides, 15-40 nucleotides, 15-35 nucleotides, 15-30 nucleotides, 15-25 nucleotides, 18-45 nucleotides, 18-40 nucleotides, 18-35 nucleotides, 18-30 nucleotides, or 18-25 nucleotides. Particularly, the length of the design criteria may be 15-40 nucleotides, 16-40 nucleotides, 17-40 nucleotides, 18-40 nucleotides, 15-35 nucleotides, 16-35 nucleotides, 17-35 nucleotides, 18-35 nucleotides, 15-30 nucleotides, 16-30 nucleotides, 17-30 nucleotides, 18-30 nucleotides, 18-25 nucleotides, or 17-25 nucleotides.

Among the design criteria, the criterion for a mononucleotide $(G)_n$ run sequence is exclusion of a mononucleotide $(G)_n$ run (n is, for example, at least 3 or 4).

Where the primer is a DPO primer developed by the present applicant (see U.S. Pat. No. 8,092,997), descriptions for the $T_m$ and the length of the DPO primer disclosed in the patent publication may be presented as the design criteria.

More particularly, the primer design criteria include at least two of the above criteria, more particularly at least three.

The above-described criteria may be used not only as design criteria of probes and primers of the first oligonucleotide candidate group but also as criteria for selecting suitable oligonucleotides. For example, the first oligonucleotide candidate group may be provided by using only a length design criterion and then suitable oligonucleotides from the first oligonucleotide candidate group may be selected based on the above-described criteria in a suitable step, for example, before evaluating a target-coverage after providing the first oligonucleotide candidate group or when providing the third oligonucleotide candidate group).

Step: Providing Reference Nucleotide Sequences (120)

At least one reference nucleotide sequence with sequence similarity to the first selected nucleotide sequence of the target nucleic acid molecule is provided. Providing the reference nucleotide sequence may be performed before, simultaneously with, or after providing the first oligonucleotide candidate group.

The term "sequence similarity" used herein with referring to the first selection nucleotide sequence and the reference nucleotide sequence means a measure of the relationship between two sequences of comparison. In the present specification, the term "sequence similarity" has meanings encompassing sequence similarity, sequence identity and sequence homology that are well known to one of skill in the art. Particularly the sequence similarity may be obtained by optimally aligning two sequences to be compared and evaluating the degree of matching of the two sequences.

Various methods and algorithms for alignment are described in Smith and Waterman, *Adv. Appl. Math.* 2:482 (1981); Needleman and Wunsch, *J. Mol. Bio.* 48:443(1970); Pearson and Lipman, *Methods in Mol. Biol.* 24: 307-31 (1988); Higgins and Sharp, *Gene* 73:237-44(1988); Higgins and Sharp, *CABIOS* 5:151-3(1989); Corpet et al., *Nuc. Acids Res.* 16: 10881-90 (1988); Huang et al., *Comp. Appl. BioSci.* 8:155-65(1992) and Pearson et al., *Meth. Mol. Biol.* 24:307-31(1994). The NCBI Basic Local Alignment Search Tool (BLAST) (Altschul et al., *J. Mol. Biol.* 215:403-10(1990)) is accessible from NCBI (National Center for Biological Information) and may be used in conjunction with sequence analysis programs such as blastn, blastp, blasm, blastx, tblastn and tblastx on the Internet. BLSAT is available at http://www.ncbi.nlm.nih.gov/BLAST/. A comparison of sequence similarity using this program may be found at http://www.ncbi.nlm.nih.gov/BLAST/blast_help.html.

According to an embodiment of the present invention, the at least one reference nucleotide sequence showing sequence similarity to the first selected nucleotide sequence of the target nucleic acid molecule is a nucleic acid molecule having the same gene name as the target nucleic acid molecule (for example, HPV type 16 L1 gene). More particularly, the target nucleic acid molecule is a nucleic acid molecule that exhibits genetic diversity, the first selected nucleotide sequence is one of nucleotide sequences of the nucleic acid molecule and at least one reference nucleotide sequence is at least one of the remaining sequences among the nucleotide sequences. For example, there are a number of sequences known as nucleotide sequences of the L1 gene of HPV type 16 that exhibit genetic diversity, one of which may be used as the first selected nucleotide sequence and at least one of the remaining sequences may be used as the reference nucleotide sequence.

According to one embodiment of the present invention, the at least one reference nucleotide sequence showing sequence similarity to the first selected nucleotide sequence of the target nucleic acid molecule is derived from an organism identical to an organism from which the first selected nucleotide sequence is derived; wherein the identical organism is identical in a hierarchy level including genus, species, subspecies, type, subtype and serotype.

For example, when a certain species of bacteria or virus is to be detected or screened, the first selection nucleotide sequence and the reference nucleotide sequence comprise sequences for the same gene found in the certain species.

According to the present invention, the reference nucleotide sequence comprises substantially all of the nucleotide sequences which exhibit sequence similarity to the first selected nucleotide sequence. For example, all nucleotide sequences uploaded to GenBank as HPV type 16 L1 gene may be used as reference nucleotide sequences.

Alternatively, the reference nucleotide sequence comprises sequences that satisfy a selection criterion among nucleotide sequences that exhibit sequence similarity to the first selected nucleotide sequence.

According to an embodiment, the at least one reference nucleotide sequence showing sequence similarity is a nucleotide sequence satisfying at least one of the following criteria: (i) a sequence identity of 70% or more (more particularly, 80% or more, more particularly, 90% or more) to the first selected nucleotide sequence of the target nucleic acid molecule; and (ii) for the first selected nucleotide sequence of the target nucleic acid molecule, a sequence coverage value of 30% or more (more particularly, 40% or more, more particularly, 50% or more) and (the sequence coverage value minus the sequence identity) of less than 10 (more particularly, less than 8, more particularly, less than 7, more particularly, less than 6, more particularly, less than 5).

The term "sequence identity" used herein with referring to the first selection nucleotide sequence and the reference nucleotide sequence means the amount of characters which match exactly between two different sequences to be compared, based on the first selected nucleotide sequence. The standard for calculating sequence identity is the first selection nucleotide sequence. For example, where the length of the first selected nucleotide sequence is 100 nucleotides, the length of the reference nucleotide sequence is 70 nucleotides and there are two mismatches, the sequence identity of the reference nucleotide sequence is 68%. Where the length of the first selected nucleotide sequence is 100 nucleotides, the length of the reference nucleotide sequence is 120 nucleotides and the reference nucleotide sequence comprises all of the first selected nucleotide sequence, the sequence identity of the reference nucleotide sequence is 100%. When determining sequence identity, gap, insertion and deletion may be considered as mismatches.

According to one embodiment of the present invention, the at least one reference nucleotide sequence showing sequence similarity is a nucleotide sequence not satisfying the following.exclusion criterion: a nucleotide sequence in which N (any nucleotide) is 3% or more (more particularly, 4% or more, more particularly, 5% more). In sequences that have been already sequenced, portions not sequenced are generally denoted by N. Accordingly, the larger the ratio of N, the less reliable the sequence. Therefore, the above-mentioned exclusion criteria may be applied.

Step: Providing a Second Oligonucleotide Candidate Group (130)

A second oligonucleotide candidate group is provided by using the first oligonucleotide candidate group. This step may be also referred to as (i) selecting oligonucleotides of the first oligonucleotide candidate group; and/or (ii) modifying with a degenerate base and/or a universal base to provide a second oligonucleotide candidate group with higher target-coverage than the first oligonucleotide candidate group.

Since the first oligonucleotide candidate group is provided in consideration of only the first selected nucleotide sequence, the first oligonucleotide candidate group generally may be a set of oligonucleotides containing a plurality of oligonucleotides with no predetermined (or desired) target-coverage for the first selected nucleotide sequence and at least one reference nucleotide sequence. Therefore, it is not suitable to directly obtain oligonucleotides (i.e., a third oligonucleotide candidate group) from the first oligonucleotide candidate group to detect actually the target nucleic acid molecule in the sample. The provision of the second oligonucleotide candidate group allows for selection or modification of certain oligonucleotides among the oligonucleotides of the first oligonucleotide candidate group, enabling to more efficiently provide the third oligonucleotide candidate group.

In the present invention, the second oligonucleotide candidate group may be provided by at least one of the following two ways.

Step (a-1)

From the first oligonucleotide candidate group, at least one oligonucleotide showing a predetermined target-coverage for the first selected nucleotide sequence and the at least one reference nucleotide sequence is selected to provide the second oligonucleotide candidate group comprising the at least one oligonucleotide.

The step (a-1) is carried out by selecting an appropriate oligonucleotide without modifying the oligonucleotide of the first oligonucleotide candidate group.

For example, the second oligonucleotide candidate group may be provided by selecting at least one oligonucleotide showing a predetermined target-coverage (e.g., 80% or more, 85% or more, 90% or more, 95% or more, or 100% target-coverage) for the first selected nucleotide sequence and the at least one reference nucleotide sequence.

The step (a-1) is suitable for providing oligonucleotides used to detect genes of an organism having a lower genetic diversity such as bacteria.

Particularly, at least one oligonucleotide with 100% target-coverage for the first selection nucleotide sequence and the at least one reference nucleotide sequence may be selected to provide the second oligonucleotide candidate group.

Meanwhile, a target-coverage of less than 100% may be ascribed by reference nucleotide sequences having a deleted region. That is, some of reference nucleotide sequences may have a deletion in a region where oligonucleotides are hybridized and therefore a target-coverage of the oligonucleotides cannot reach 100%. In this case, the oligonucleotides may be suitable as the second oligonucleotide candidate group. In one embodiment of the present invention, the target coverage of oligonucleotides may be calculated considering only the sequence of the remaining regions except for a deletion region in the reference nucleotide sequences.

Particularly, the second oligonucleotide candidate group may be provided by selecting oligonucleotides which (i) exhibit 100% target-coverage and/or (ii) exhibit a target-coverage from less than 100% to 60% (particularly, from less than 100% to 70%, more particularly, from less than 100% to 80%, more particularly, from less than 100% to 90%) due to reference nucleotide sequences having a deleted region.

Step (a-2)

Alternatively, the second oligonucleotide candidate group may be provided as follows:

In the first oligonucleotide candidate group, at least one base of at least one oligonucleotide showing a target-coverage of less than 100% for the first selected nucleotide sequence and at least one reference nucleotide sequence is replaced with a degenerate base and/or a universal base to provide a modified oligonucleotide with increased target-coverage, thereby providing the second oligonucleotide candidate group. The second oligonucleotide candidate group comprises comprising the modified oligonucleotide.

In the step (a-2), the at least one oligonucleotide of the first oligonucleotide candidate group is modified.

According to one embodiment of the present invention, the oligonucleotides to be modified are oligonucleotides whose target-coverage are less than 100% and are enabled to be increased by replacing with a degenerate base and/or a universal base.

For example, oligonucleotides representing 100% target-coverage for the first selected nucleotide sequence and the reference nucleotide sequences are not subject to modification. In addition, oligonucleotides which exhibit less than 100% target-coverage due to reference nucleotide sequences having a deleted region are not subject to modification because their target-coverages are not increased by the modification.

Furthermore, where the number of degenerate bases and/or universal bases to be introduced is limited and the bases in more than the limited number have to be introduced into oligonucleotides to increase their target-coverage, such oligonucleotides are also not subject to modification. For example, assumed that the number of degenerate bases and/or universal bases to be introduced is limited to no more, than 3, the number of the reference nucleotide sequences is 9, the target coverage of an oligonucleotide is 90% and one reference nucleotide sequence not to be covered has four mutations in a probing region, four degenerate bases and/or universal bases need to increase target-coverage. Such oligonucleotides are also excluded from the modification.

According to an embodiment, the modified oligonucleotide with increased target-coverage in the step (a-2) are oligonucleotides prepared in such a manner that at least one base of each of some or all (more particularly, all) oligonucleotides in the first oligonucleotide candidate group whose target-coverage is enabled to be increased by introduction of the degenerate base and/or the universal base is replaced with the degenerate base and/or the universal base.

Alternatively, the modified oligonucleotide with increased target-coverage in the step (a-2) are oligonucleotides prepared in such a manner that at least one base of each of some or all (more particularly, all) oligonucleotides in the first oligonucleotide candidate group whose target-coverage is enabled to show a predetermined target-coverage by introduction of the degenerate base and/or the universal base is replaced with the degenerative base and/or the universal base. The predetermined target-coverage is, for example, 30% or more, 40% or more, 50% or more, 60% or more, 70% or more, 80% or more, 90% or more, 95% or more or 100%.

The number of degenerate bases and/or universal bases to. be introduced in the above two embodiments is particularly 25% or less, 20% or less, 18% or less, 16% or less, 14% or less, 12% or less, 10% or less, 8% or less, or 6% or less based on a total length of a portion hybridized with the target nucleic acid molecule in the oligonucleotide. The number of degenerate bases and/or universal bases to be introduced in the above two embodiments is particularly 7 or less, 5 or less, 4 or less, or 3 or less.

According to an embodiment of the present invention, the modified oligonucleotide with increased target-coverage in the step (a-2) are oligonucleotides prepared in such a manner that modified oligonucleotides having the highest target-coverage by introducing the least number of the degenerate base and/or the universal base are selected among modified oligonucleotides provided by introducing the degenerate base and/or the universal base of no more than a predetermined number into at least two oligonucleotides of the first oligonucleotide candidate group.

For instance, when the number of degenerate bases and/or universal bases to be introduced is limited to not more than 3, modified oligonucleotides are prepared to show the highest target-coverage for the first selected nucleotide sequence and the at least reference nucleotide sequence by introducing 3 or less of the degenerate base and/or the universal base. For example, 3 or less of degenerate bases are introduced into an oligonucleotide of the first oligonucleotide candidate group showing 80% target-coverage. In this case, where 95% target-coverage is given by introducing degenerate bases into 5, 8 and 10 positions and 99% target-coverage is given by introducing degenerate bases into 5, 8, 13 and 18 positions, modified oligonucleotides having 95% target-coverage are selected as the second candidate group.

The oligonucleotides into which degenerate bases and/or universal bases of no more than a predetermined number are introduced are some or all oligonucleotides whose target-coverage shows less than 100% and is enabled to be increased by replacing with the degenerate bases and/or the universal bases. Alternatively, the oligonucleotides into which degenerate bases and/or universal bases of no more than a predetermined number are introduced are some or all oligonucleotides showing a predetermined target-coverage by the introduction of degenerate bases and/or universal bases.

Alternatively, the modified oligonucleotide with increased target-coverage in the step (a-2) are oligonucleotides prepared in such a manner that modified oligonucleotides having the highest target-coverage by introducing the least number of the degenerate base and/or the universal base are selected among modified oligonucleotides provided by introducing the degenerate base and/or the universal base of a predetermined number into at least two oligonucleotides of the first oligonucleotide candidate group. For example, the modified oligonucleotides with increased target-coverage in step (a-2) includes modified oligonucleotides having the highest target-coverage among modified oligonucleotides provided by introducing one degenerate base into at least two oligonucleotides of the first oligonucleotide candidate group and modified oligonucleotides having the highest target-coverage among modified oligonucleotides provided by introducing two degenerate bases into at least two oligonucleotides of the first oligonucleotide candidate group.

Particularly, the predetermined number of the degenerate bases and/or universal bases to be introduced in this embodiment is particularly 25% or less, 20% or less, 18% or less, 16% or less, 14% or less, 12% or less, 10% or less, 8% or less or 6% or less based on a total length of a portion hybridized with the target nucleic acid molecule in the oligonucleotide. The predetermined number of the degenerate bases and/or universal bases to be introduced in this embodiment is particularly 7 or less, 5 or less, 4 or less, or 3 or less.

The second oligonucleotide candidate group provided by this embodiment comprises modified oligonucleotides each of which shows the highest target-coverage by modification of each of the at least one oligonucleotide of the first oligonucleotide candidate group. For example, where there are 100 oligonucleotides to be modified, the second oligonucleotide candidate group comprises modified oligonucleotides each of which shows the highest target-coverage by modification of each of the 100 oligonucleotides.

Particularly, the second oligonucleotide candidate group comprises modified oligonucleotides each of which shows the highest target-coverage by modification of each of some or all (particularly, all) oligonucleotides in the first oligonucleotide candidate group whose target-coverage shows less than 100% and is enabled to be increased by replacing with degenerate bases and/or universal bases. Alternatively, the second oligonucleotide candidate group comprises modified oligonucleotides each of which shows the highest target-coverage by modification of each of some or all (particularly, all) oligonucleotides in the first oligonucleotide candidate group showing a predetermined target-coverage by the introduction of degenerate bases and/or universal bases.

According to one embodiment of the present invention, the present invention may be carried out by a combination of the steps (a-1) and (a-2). For example, the step (a-1) is performed before or after the step (a-2) to provide the second oligonucleotide candidate group. For example, oligonucleotides with 100% target-coverage prior to the modification are selected to provide the second oligonucleotide candidate group. In this case, the second oligonucleotide candidate group comprises oligonucleotides with 100% target-coverage and modified oligonucleotides.

The second oligonucleotide candidate group provided by the step (a-2) typically comprises modified oligonucleotides. According to an embodiment, the second oligonucleotide candidate group provided by the step (a-2) further comprises at least one of the followings: (i) an oligonucleotide showing the target coverage of 100% and (ii) an oligonucleotide whose target-coverage falls within the predetermined target-coverage and is not increased by replacing with the degenerate base and/or the universal bases.

According to one embodiment of the present invention, the method further comprises, before providing the second oligonucleotide candidate group, evaluating a target-coverage of the first oligonucleotide candidate group by analyzing whether the first oligonucleotide candidate group is hybridized with the first selected nucleotide sequence and at least one reference nucleotide sequence.

The term used herein "target-coverage" refers to a proportion of the first selected nucleotide sequence and the at least one reference nucleotide sequence with which a probe and/or primer of the first oligonucleotide candidate group is hybridized. For example, where the probe of the first oligonucleotide candidate group is hybridized with 80 sequences among 100 total sequences of first selected nucleotide sequences and reference nucleotide sequences, it may be evaluated to show 80% target-coverage.

More particularly, the term "target-coverage" refers to a proportion of the first selected nucleotide sequence and at least one reference nucleotide sequence that are 100% matched to a sequence of a probe and/or primer of the first oligonucleotide candidate group.

The expression used herein "analyzing whether hybridization occurs or not" with referring to the evaluation of a target-coverage includes analyzing the possibility of hybridization between two sequences. More particularly, the expression "analyzing whether hybridization occurs or not" includes analyzing whether the first selection nucleotide sequence and at least one reference nucleotide sequence are 100% matched with a sequence of a probe and/or primer of the first oligonucleotide candidate group.

According to an embodiment, the first oligonucleotide candidate group for target-coverage evaluation comprises initial-selected oligonucleotides selected by a predetermined selection criterion prior to evaluating target-coverage or the first oligonucleotide candidate group not to be initial-selected.

For example, the first oligonucleotide candidate group is subjected to an initial-selection with regard to at least one of the selection criteria applied to the second oligonucleotide candidate group to provide the third oligonucleotide candidate group described below, and the target-coverage may be evaluated for the sorted-in (or filtered-in) oligonucleotides. Alternatively, the target-coverage may be evaluated for all of the first oligonucleotide candidates without such selection.

According to one embodiment of the present invention, when performing the step (a-1), the target-coverage of the first oligonucleotide candidate group for the first selected nucleotide sequence and the at least one reference nucleotide sequence is evaluated, and at least one oligonucleotide showing the predetermined target-coverage are selected to provide the second oligonucleotide candidate group.

According to one embodiment of the present invention, when performing the step (a-2), (i) the target-coverage of the first oligonucleotide candidate group for the first selected nucleotide sequence and the at least one reference nucleotide sequence is evaluated, (ii) an oligonucleotide showing the target coverage of 100% and/or an oligonucleotide whose target-coverage is less than 100% and is not increased by replacing with the degenerate base and/or the universal base are selected to provide the second oligonucleotide candidate group, and (iii) the second oligonucleotide candidate group is provided by replacing with a degenerate base and/or a universal base at least one base of at least one oligonucleotide whose target-coverage is less than 100% and is increased by replacing with the degenerate base and/or the universal base to provide a modified oligonucleotide with increased target-coverage.

In the present specification, the expression "evaluating a target-coverage of the first oligonucleotide candidate group" may be expressed as analyzing sequence diversity of the first selected nucleotide sequence and at least one reference nucleotide sequence with regard to a region of the first selected nucleotide sequence with which the first oligonucleotide candidate group is hybridized. That is, since the first oligonucleotide candidate group includes sequences that are matched with the first selected nucleotide sequence, evaluating the target-coverage of the first oligonucleotide candidate group may give information on sequence diversity of the first selected nucleotide sequence and at least one reference nucleotide sequence with regard to a region of the first selected nucleotide sequence (i.e., probing region or priming region) with which the first oligonucleotide candidate group is hybridized.

Therefore, according to another embodiment of the present invention, evaluating the target-coverage is performed by analyzing sequence diversity of the first selected nucleotide sequence and at least one reference nucleotide sequence (e.g., patterning sequence diversity) and comparing the analyzed sequence diversity with the first oligonucleotide candidate group to evaluate the target-coverage of the first oligonucleotide candidate group for the first selected nucleotide sequence and the at least one reference nucleotide sequence.

According to one embodiment of the present invention, when performing the step (a-2), (i) the sequence diversity of the first selected nucleotide sequence and the at least one reference nucleotide sequence is analyzed, (ii) at least one base of at least one oligonucleotide of the first oligonucleotide candidate group with a target-coverage of less than 100% for the first selected nucleotide sequence and at least one reference nucleotide sequence is selected in consideration of the analyzed sequence diversity, and the second oligonucleotide candidate group is provided by replacing the selected at least one base with a degenerate base and/or a universal base to provide a modified oligonucleotide with increased target-coverage. In particular, the selection of at least one base of the oligonucleotide to be modified is done such that a target-coverage as high as possible is obtained using as few degenerate bases and/or universal bases as possible.

According to an embodiment, when performing the step (a-2), (i) the sequence diversity of the first selected nucleotide sequence and the at least one reference nucleotide sequence is analyzed, (ii) at least one base of at least one oligonucleotide of the first oligonucleotide candidate group with less than 100% target-coverage for the first selected nucleotide sequence and at least one reference nucleotide sequence is selected in consideration of the analyzed sequence diversity to show the highest target-coverage by the introduction of a degenerate base and/or a universal base of no more than a predetermined number into the at least one oligonucleotide, and the second oligonucleotide candidate group is provided by replacing the selected at least one base with the degenerate base and/or the universal base to provide a modified oligonucleotide with increased target-coverage.

The degenerate bases to be introduced include the various degenerate bases known in the art as follows: R: A or G; Y: C or T; S: G or C; W: A or T; K: G or T; M: A or C; B: C or G or T; D: A or G or T; H: A or C or T; V: A or C or G; N: A or C or G or T. When an oligonucleotide is modified by introduction of the degenerate base, the sequence description of the modified oligonucleotide is different from that of the oligonucleotide before modification but the modified oligonucleotide comprises the oligonucleotide before modification. Accordingly, the term "modified oligonucleotide" used in connection with the introduction of degenerate bases means a set of oligonucleotides which comprises all oligonucleotides including oligonucleotide before modification represented by the sequence description of modified oligonucleotides.

The universal base to be introduced include the following various universal bases known in the art: deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'O-methoxyethyl nebularine, 2'-O-methoxyethyl 5-nitroindole, 2'-O-methoxyethyl 4-nitro-benzimidazole, 2'-O-methoxyethyl 3-nitropyrrole, and combinations thereof.

More particularly, the universal base is deoxyinosine, inosine, or combinations thereof.

According to one embodiment of the present invention, the base used to increase a target-coverage is a degenerate base. Degenerate oligonucleotides include a plurality of oligonucleotides represented by degenerate oligonucleotide sequences. Unless especially stated otherwise herein, degenerate oligonucleotides refer to a subgroup comprising a plurality of oligonucleotides represented by degenerate oligonucleotide sequences, rather than a single oligonucleotide.

Step: Providing a Third Oligonucleotide Candidate Group (140)

A third oligonucleotide candidate group is provided by selecting oligonucleotide(s) depending on a predetermined selection criterion from the second oligonucleotide candidate group. The third oligonucleotide candidate group is used for detecting the target nucleic acid molecule in the sample.

The selection of suitable oligonucleotides in the second oligonucleotide candidate group may be carried out in accordance with various selection criteria.

According to one embodiment of the present invention, the predetermined selection criterion for selecting the oligonucleotide from the second oligonucleotide candidate group to provide the third oligonucleotide candidate group is at least one criterion selected from the group consisting of: (i) the number or proportion of the degenerate base and/or the universal base used; (ii) an actual use rate of oligonucleotide patterns generated by introduction of the degenerate base; (iii) an oligonucleotide pattern number generated by introduction of the degenerate base; (iv) the target-coverage for the first selected nucleotide sequence of the target nucleic acid molecule and at least one reference nucleotide sequence; (v) for the tagging probe described above, the non-complementarity level of the first tagging part; (vi) when the oligonucleotide forms a homodimer, the number or proportion of consecutive nucleotides involved in the formation of the homodimer; (vii) a hairpin structure-forming free energy value ($\Delta G$ value); (viii) a $T_m$ value; (ix) a GC content; and (x) a length.

Among the selection criteria, the proportion of the degenerate base and/or the universal base used is the proportion of the degenerate base or the universal base among the total nucleotides of the oligonucleotide (for the tagging probe, the targeting portion) into which the degenerate base or the universal base is introduced. The actual use rate of oligonucleotide patterns generated by introduction of the degenerate base refers to the number of oligonucleotide types having sequences that are actually matched and hybridized to the first selected nucleotide sequence of the target nucleic acid molecule and at least one reference nucleotide sequence, among the total oligonucleotide types generated by introduction of the degenerate base. For example, when two degenerate bases B (C or G or T) and D (A or G or T) are introduced into a probe to increase the target-coverage to 100%, the total number of oligonucleotides types generated is 9 types. In addition, when the first selected nucleotide sequence of the target nucleic acid molecule and at least one reference nucleotide sequence comprises six types of sequences, the actual use ratio is "(6/9)×100".

Meanwhile, a few of the selection criteria such as (viii) a $T_m$ value, (ix) a GC content and (x) a length may be adopted as design criteria of the oligonucleotide described above and may not be adopted as selection criteria.

There are two methods for selecting oligonucleotides in accordance with the selection criteria: According to the first method, the selection is performed by ranking the oligonucleotides in accordance with the selection criterion and selecting oligonucleotides ranked above a predetermined rank. According to the second scheme, the selection is carried out by selecting oligonucleotides satisfying the cut-off value given to the selection criterion.

In the first method, the rank in accordance with the selection criteria is performed as follows: (i) the number or proportion of the degenerate base and/or the universal base used: the smaller the number or proportion used, the higher the rank; (ii) an actual use rate of oligonucleotide patterns generated by introduction of the degenerate base: the higher the rate, the higher the rank; (iii) an oligonucleotide pattern number generated by introduction of the degenerate base: the lower the number of pattern, the higher the rank; (iv) the target-coverage for the first selected nucleotide sequence of the target nucleic acid molecule and at least one reference nucleotide sequence: the higher the target-coverage, the higher the rank; (v) for the tagging probe described above, the non-complementarity level of the first tagging part: the higher the non-complementarity level, the higher the rank; (vi) when the oligonucleotide forms a homodimer, the number or proportion of consecutive nucleotides involved in the formation of the homodimer: the smaller the number or proportion, the higher the rank; (vii) a hairpin structure-forming free energy value ($\Delta G$ value): the larger the $\Delta G$ value, the higher the rank.

The third oligonucleotide candidate group may be provided by ranking the oligonucleotides in accordance with the ranking method and selecting oligonucleotides (for example, oligonucleotides included in upper 50%) ranked above a predetermined rank.

According to the second method, the cut-off value given to the selection criterion may be determined empirically. For example, (i) the number or proportion of the degenerate base and/or the universal base used: three bases as cut-off values (or 15%); (ii) an actual use rate of oligonucleotide patterns generated by introduction of the degenerate base: cut-off value 60%; (iii) an oligonucleotide pattern number generated by introduction of the degenerate base: 12 patterns as cut-off values; (iv) the target-coverage for the first selected nucleotide sequence of the target nucleic acid molecule and at least one reference nucleotide sequence: cut-off value 100%; (v) for the tagging probe described above, the non-complementarity level of the first tagging part: a certain numericized value of unfavorability as cut-off value; (vi) when the oligonucleotide forms a homodimer, the number or proportion of consecutive nucleotides involved in the formation of the homodimer: cut-off value 55%; (vii) a hairpin structure-forming free energy value ($\Delta G$ value): cut-off value −3.0 kcal/mol; (viii) a $T_m$ value: cut-off value 55° C.; (ix) a GC content: cut-off value 35%; and (x) a length: 15 nucleotides as cut-off value.

According to an embodiment, the selection criteria may include a plurality of selection criteria [particularly, selection criteria (i)-(iii), more particularly selection criteria (i)-(iv), more particularly selection criteria (i)-(v), more particularly selection criteria (i)-(vi), more particularly selection criteria (i)-(vii)], and the third oligonucleotide candidate group is provided by selecting oligonucleotides for each of a plurality of selection criteria. In this case, all oligonucleotides selected for each of the plurality of selection criteria or common oligonucleotides in oligonucleotides selected for each of the plurality of selection criteria may be provided as the third oligonucleotide candidate group.

For example, where oligonucleotides are selected according to the first method, the oligonucleotides are ranked for each of the selection criteria (i)-(vii) and the oligonucleotides belonging to the top 50% in each of the selection criteria may be selected to provide the third oligonucleotide candidate group.

According to an embodiment, an oligonucleotide at the highest rank or oligonucleotides above a certain rank for at least one of the upper selection criteria may be provided as a third oligonucleotide candidate group, and the third oligonucleotide candidate group is used for detecting of a target nucleic acid molecule in a sample.

According to one embodiment of the present invention, when some sequences from the second oligonucleotide candidate are selected to provide the third oligonucleotide candidate group, a degenerate oligonucleotide comprising a plurality of oligonucleotides is selected as the degenerate oligonucleotide itself. Particularly, the degenerate oligonucleotide comprises a plurality of oligonucleotides, and the selection does not done for some of the plurality of oligonucleotides represented by the degenerate oligonucleotide but for the degenerate oligonucleotide per se.

In the above embodiment, when evaluating a degenerate oligonucleotide for the selection criteria (vi), the selection is performed based on an oligonucleotide having the largest number or proportion of consecutive nucleotides involved in the formation of the homodimer among a plurality of oligonucleotides represented by the degenerate oligonucleotide. Alternatively, the selection may be made based on the average number or proportion of a plurality of oligonucleotides represented by the degenerate oligonucleotide. The evaluation of such degenerate oligonucleotide for the selection criteria is also applicable to other items, for example, in the case of a hairpin structure-forming $\Delta G$ value, the selection is performed based on the smallest $\Delta G$ value-possessing oligonucleotide among a plurality of oligonucleotides represented by a degenerate oligonucleotide. Alternatively, the selection may be made based on the average $\Delta G$ value of a plurality of oligonucleotides.

According to one embodiment, the selected third oligonucleotide candidate group as described above may be used for detecting of a target nucleic acid molecule in a sample, but additional selection may be made to select more suitable oligonucleotides.

According to one embodiment of the present invention, the method further comprises assigning ranks to the oligonucleotides of the third oligonucleotide candidate group in accordance with at least one of the following priority items:

(i) the target-coverage for the first selected nucleotide sequence of the target nucleic acid molecule and at least one reference nucleotide sequence; wherein the higher the target-coverage, the higher the priority, (ii) an actual use rate of oligonucleotide patterns generated by introduction of the degenerate base; wherein the higher the actual use ratio, the higher the priority, (iii) the number or proportion of the degenerate base and/or the universal base used; wherein the smaller the number or proportion of the degenerate base and/or the universal base, the higher the priority, (iv) when the oligonucleotide forms a homodimer, the number or proportion of consecutive nucleotides involved in the formation of the homodimer; wherein the smaller the number or proportion, the higher the priority, (v) a hairpin structure-forming free energy value ($\Delta G$ value); wherein the higher the free energy value, the higher the priority, (vi) a length; wherein the shorter the length, the higher the priority, (vii) for the tagging probe described above, the non-complementarity level of the first tagging part; wherein the higher the non-complementarity level, the higher the priority.

According to the present invention, oligonucleotides of the third oligonucleotide candidate group are ranked with regard to at least one (particularly, priority item (i)), particularly at least 2, more particularly at least 3, more particularly at least 4, more particularly at least 5, more particularly at least 6 priority items.

According to an embodiment, the at least two priority items differ from each other in terms of criticality and the method further comprises selecting at least one oligonucleotide from the oligonucleotides of the third oligonucleotide candidate group in accordance with ranks in the at least two priority items with considering the criticality.

There are two methods for selecting a more suitable oligonucleotide from the third oligonucleotide candidate group:

According to the first method, the at least two priority items differ from each other in terms of criticality and a top-most oligonucleotide may be selected by ranking for the priority item having the highest criticality (e.g., priority item (i)).

When a plurality of top-most oligonucleotides are present in the priority item with the highest criticality, the oligonucleotide having the highest rank is selected by comparing ranks in a priority item with just lower criticality than the highest criticality.

For example, if the criticality of the priority items is in the order of (i)-(iii) and there are 5 top-most oligonucleotides in the priority item (i), the ranks of the 5 top-most oligonucleotides is compared in the priority item (ii). If the ranks in the priority item (ii) are also the same, the oligonucleotide having the highest rank is selected by comparing ranks in the priority item (iii).

According to the second method, the total score of each oligonucleotide may be obtained by assigning different weights to priority items and assigning scores to values (or ranges of values) in each priority item. Taking this calculated total score into consideration, a more suitable oligonucleotide may be selected from the third oligonucleotide candidate group.

Where the detection of a target nucleic acid molecule is performed using an appropriate combination of a probe and a primer such as PTOCE and TaqMan methods, partnerships or collaboration between the probe and the primer in the detection of the target nucleic acid molecule are important although excellent characteristics of the probe and the primer itself are also important.

For example, primers should be located upstream and downstream with regard to the selected probe, and be capable of forming an amplicon having an appropriate size (particularly, 100-1000, more particularly 200-800, still more particularly 300-700, still much more particularly 300-500, most particularly 300-400 nucleotides).

A primer should have no interference with a probe. A representative of such interference is dimer formation. Although the primer and the probe have excellent properties, the primer may not be appropriate when it forms a heterodimer with the probe.

Particularly, a primer has a lower $T_m$ value than a probe. For example, the $T_m$ value of the primer may be in the range of [55° C. to ($T_m$ of the probe minus 10° C.) ° C.] in relation to the probe.

According to an embodiment, the prioritized oligonucleotides are probes, a top-most probe is selected from the prioritized probes and a primer suitable for the top-most probe is selected. The term "suitable" means possession of at least one of the following characteristics: with respect to the selected probe, a primer and the probe do not form a heterodimer, primers form an amplicon of the desired size, and a primer has a $T_m$ value of [55° C. to ($T_m$ of the probe minus 10° C.) ° C.].

For example, where the third oligonucleotide group comprising probes and primers selected is provided by the present invention, a top-most probe is selected and a top-most primer suitable for this probe is selected. If a primer suitable for the top-most probe is absent in the third oligonucleotide candidate group, a suitable primer is re-selected for a probe with just lower rank than the top-most probe. A combination of the re-selected primer and the probe with just lower rank than the top-most probe is used as oligonucleotides for detecting a target nucleic acid molecule in a sample.

In the present invention, a primer may be selected in accordance with the following suitability with respect to a probe: first, when the primer forms a heterodimer with the probe and the proportion of consecutive nucleotides involved in the formation of the homodimer is 65% or less (particularly, 60% or less, more particularly 55% or less, still more particularly 50% or less, still much more particularly 40% or less), it may be determined that the suitability is satisfied. Second, when the primer forms an amplicon having an appropriate size (particularly, 100-1000, more particularly 200-800, still more particularly 300-700, still much more particularly 300-500, most particularly 300-400 nucleotides), it may be determined that the suitability is satisfied. In addition, the second item may be included in design criteria when designing an oligonucleotide to provide the first oligonucleotide candidate group. Third, where a $T_m$ value of a primer is in the range of [55° C. to ($T_m$ of the probe minus 10° C.) ° C.], it may be determined that the suitability is satisfied. The third item may be included in design criteria when designing an oligonucleotide to provide the first oligonucleotide candidate group.

The term used herein "preparing or preparation" with referring to oligonucleotides includes provision of an oligonucleotide sequence as well as manufacture of an oligonucleotide molecule. The present invention provides the third oligonucleotide candidate group or actual use oligonucleotide for detecting a target nucleic acid molecule in a sample. Where a degenerate oligonucleotide is provided, only sequences actually matched and hybridized to the first selected nucleotide sequence of the target nucleic acid molecule and at least one reference nucleotide sequence may be prepared (e.g., synthesized and supplied) among a plurality of oligonucleotides represented by the degenerate oligonucleotide.

II. Storage Medium, Device and Program

In another aspect of this invention, there is provided a computer readable storage medium containing instructions to configure a processor to perform a method for preparing oligonucleotides for detecting a target nucleic acid molecule in a sample, the method comprising:

designing oligonucleotides for detecting the target nucleic acid molecule in the sample using information related to the target nucleic acid molecule to provide a first oligonucleotide candidate group; wherein the information related to the target nucleic acid molecule comprises a first selected nucleotide sequence of the target nucleic acid molecule and the first oligonucleotide candidate group comprises a probe and/or a primer comprising a nucleotide sequence complementary to the first selected nucleotide sequence of the target nucleic acid molecule;

providing at least one reference nucleotide sequence with sequence similarity to the first selected nucleotide sequence of the target nucleic acid molecule;

providing a second oligonucleotide candidate group using the first oligonucleotide candidate group; wherein the provision is performed by at least one of the followings;

(a-1) in the first oligonucleotide candidate group, selecting at least one oligonucleotide showing a predetermined target-coverage for the first selected nucleotide sequence and the at least one reference nucleotide sequence to provide a second oligonucleotide candidate group comprising the at least one oligonucleotide; and (a-2) in the first oligonucleotide candidate group, replacing with a degenerate base and/or a universal base at least one base of at least one oligonucleotide showing a target-coverage of less than 100% for the first selected nucleotide sequence and at least one reference nucleotide sequence to provide a modified oligonucleotide with increased target-coverage, thereby providing the second oligonucleotide candidate group comprising the modified oligonucleotide; and selecting oligonucleotide(s) depending on a predetermined selection criterion from the second oligonucleotide candidate group to provide a third oligonucleotide candidate group; wherein the third oligonucleotide candidate group is used for detecting the target nucleic acid molecule in the sample.

In still another aspect of this invention, there is provided a computer program to be stored on a computer readable storage medium, to configure a processor to perform a method for preparing oligonucleotides for detecting a target nucleic acid molecule in a sample, the method comprising:

designing oligonucleotides for detecting the target nucleic acid molecule in the sample using information related to the target nucleic acid molecule to provide a first oligonucleotide candidate group; wherein the information related to the target nucleic acid molecule comprises a first selected nucleotide sequence of the target nucleic acid molecule and the first oligonucleotide candidate group comprises a probe and/or a primer comprising a nucleotide sequence complementary to the first selected nucleotide sequence of the target nucleic acid molecule;

providing at least one reference nucleotide sequence with sequence similarity to the first selected nucleotide sequence of the target nucleic acid molecule;

providing a second oligonucleotide candidate group using the first oligonucleotide candidate group; wherein the provision is performed by at least one of the followings;

(a-1) in the first oligonucleotide candidate group, selecting at least one oligonucleotide showing a predetermined target-coverage for the first selected nucleotide sequence and the at least one reference nucleotide sequence to provide a second oligonucleotide candidate group comprising the at least one oligonucleotide; and (a-2) in the first oligonucleotide candidate group, replacing with a degenerate base and/or a universal base at least one base of at least one oligonucleotide showing a target-coverage of less than 100% for the first selected nucleotide sequence and at least one reference nucleotide sequence to provide a modified oligonucleotide with increased target-coverage, thereby providing the second oligonucleotide candidate group comprising the modified oligonucleotide; and selecting oligonucleotide(s) depending on a predetermined selection criterion from the second oligonucleotide candidate group to provide a third oligonucleotide candidate group; wherein the third oligonucleotide candidate group is used for detecting the target nucleic acid molecule in the sample.

In another aspect of this invention, there is provided a device for preparing oligonucleotides for detecting a target nucleic acid molecule in a sample, comprising (a) a computer processor, and (b) a computer readable storage medium of the present method coupled to the computer processor.

Since the storage medium, the device and the computer program of the prevent invention are intended to perform the present methods described hereinabove in a computer, the common descriptions between them are omitted in order to avoid undue redundancy leading to the complexity of this specification.

The program instructions are operative, when performed by the processor, to cause the processor to perform the present method described above. The program instructions for performing the method of preparing the oligonucleotides may comprise the following instructions: (i) an instruction to design oligonucleotides for detecting the target nucleic acid molecule in the sample using a first selected nucleotide sequence of the target nucleic acid molecule to provide a first oligonucleotide candidate group; (ii) an instruction to provide at least one reference nucleotide sequence with sequence similarity to the first selected nucleotide sequence of the target nucleic acid molecule; (iii) an instruction to evaluate a target-coverage of the first oligonucleotide candidate group; (iv) an instruction to in the first oligonucleotide candidate group, replace with a degenerate base and/or a universal base a base of an oligonucleotide not showing a predetermined target-coverage or more to provide a modified oligonucleotide with increased target-coverage, thereby providing the second oligonucleotide candidate group; and (v) an instruction to select oligonucleotide(s) depending on a predetermined selection criterion from the second oligonucleotide candidate group to provide (e.g., displaying on output device) a third oligonucleotide candidate group.

The present method is implemented in a processor, such as a processor in a stand-alone computer, a network attached computer or a data acquisition device.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The oligonucleotides for detecting a target nucleic acid molecule in a sample may be provided in a variety of ways. For example, the sequence of the oligonucleotides may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the sequence of the oligonucleotides may be provided to a server system via a network connection (e.g., LAN, VPN, Internet, intranet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

The computer processor may be prepared in such a manner that a single processor can do several performances. Alternatively, the processor unit may be prepared in such a manner that several processors do the several performances, respectively.

The features and advantages of this invention are summarized as follows:

(a) According to conventional methods for preparing oligonucleotides for detecting a target nucleic acid molecule, particularly a target nucleic acid molecule exhibiting genetic diversity, all sequences exhibiting genetic diversity are referred to simultaneously to determine not only regions with which the oligonucleotides are hybridized but also the introduction of a degenerate base. The conventional methods are a time-consuming and labor-consuming process.

Unlike the conventional methods, the present invention provides a first oligonucleotide candidate group designed appropriately for the first selected nucleotide sequence of the target nucleic acid molecule as a standard instead of simultaneously referring to all of the sequences exhibiting the genetic diversity. Then, an optimal oligonucleotide capable of accurately detecting a target nucleic acid molecule exhibiting genetic diversity in a sample is provided by using the first oligonucleotide candidate group.

(b) In particular, the present invention may successfully provide a tagging oligonucleotide (specifically, a tagging probe) capable of detecting a target nucleic acid molecule in a sample exhibiting genetic diversity.

(c) According to an embodiment of the present invention, a probe and/or a primer capable of detecting a target nucleic acid molecule exhibiting genetic diversity in a sample may be provided by a suitable selection procedure from the first oligonucleotide candidate group having a vast amount of information.

(d) According to the present invention, when sequences showing genetic diversity are newly identified to increase a target nucleic acid sequence pool after a probe and/or a primer for detecting a target nucleic acid molecule is provided, a suitable probe and/or primer capable of covering the increased target nucleic acid sequence pool may be selected from the third oligonucleotide candidate group. Alternatively, in this case, a suitable probe and/or primer capable of covering the increased target nucleic acid sequence pool may be easily provided without changing the first oligonucleotide candidate group by only performing subsequent steps following generation of the first oligonucleotide candidate group.

(e) When the method of the present invention is implemented by a computer program, oligonucleotides for detecting a target nucleic acid molecule in a sample having a suitable sequence may be very efficiently and quickly provided.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Preparation of Oligonucleotides for Detection of the PHR1 Gene of *Candida albicans*

Information Input

The name of *Candida albicans* as a target organism, its taxonomy ID (particularly, taxonomy ID in GenBank) and PHR1 gene sequence information in length of 2026 mer as a first selected nucleotide sequence (Table 1) were used as information related to a target nucleic acid molecule.

TABLE 1

Sequence (SEQ ID: 1)
(5' to 3')

GAATTCATCGACGCCTCATTCATACTAATATAATAGGTGTTGCAACATCA
AAATCATTTCATCGCTAATACAAACATCCGAGATTAATCTTGTCCATTGG
CAATATAATTAACACCACTGCCAATACATATAAATCAAATCAGCATTAAC
TAATAGTATTTATTAATTACTTAGAAAAGCCGGGCTGCGTTTTTTTGTTT
CATTCATAGATTTACTTATTTCCATTTAACATACCAAACTACAGGTTGAA
GCCAAAAAAAATGTATTCATTAATCAAATCATTGGCCACATTTGCCACA
CTCTTTTCATTAACTTTAGCCAAGTTTGAATCGTCCACCCCACCAGTTGA
AGTTGTTGGTAACAAATTTTATTTTTCCAATAATGGGTCTCAGTTTTAAT
CAGGGGTATCGCCTATCAGCAAGATGCCGCGGGCTCAGTTTCCTCCGGTT
ACGACGCCGATCCTAATAGAAAATACAATGATCCTTTAGCCGATCGTGAC
GCTTGTAAACGTGACGTCAAGTATTTCAAAGAATCAAACACCAATACTTT
GAGAGTTTATGCTATTGACCCAGATAAGGATCATGAAGAGTGTATGAAAA
TTTTCAGTGACGCTGGTATTTACATTGTTGCTGATTTATCAGAACCAACT
GTATCGATTAACAGAAACAACCCAGAATGGAACTTGGATTTATACAAACG
TTATACAAAAGTCATTGATAAGATGCAAGAATATTCTAATGTTTTGGGAT
TTTTTGCTGGTAACGAAGTAACTAATAATCGTTCAAATACCGATGCTTCT
GCATTTGTTAAGGCTGCCATTAGAGATATGAAGAAATACATCAAGGAGTC
TGATTATAGACAAATTCCTGTTGGTTATTCATCCAATGATGACGAAGAAA
TTAGAGTCGCCATTGCCGATTATTTCTCTTGTGGTTCATTAGATGATCGT
GCTGATTTCTTTGGTATCAATATGTATGAATGGTGTGGCAAATCAACTTT
CGAAACCTCAGGTTACAAGGACAGAACTGAAGAAATCAAGAACTTGACTA
TCCCAGCCTTCTTCTCCGAATATGGATGTAATGCTAACCGTCCACGTTTG
TTCCAAGAAATTGGTACCTTGTATTCCGATAAGATGACTGATGTTTGGTC
CGGAGGTATTGTTTATATGTATTTTGAAGAGGCTAACAAATACGGTTTGG
TTCTGGTTGATGGTAATTCGGTCAAGACATTATCTGACTACAACAATTAC
AAATCAGAAATGAACAAAATAAGCCCATCCCTTGCCCATACTTCAACATT
ATCCAGTTCTGACGCCAGCAAGACTTTGCAATGTCCAGGAACTGCTGCTA
GCACTTGGAAAGCTGCAACTAATTTGCCACCAACTCCAGATGAAAGTTAC
TGTGATTGTATTTCCAAGTCATTAGAATGTGTTGTTGCTGACGATGTTGA
TAAAGAAGACTATGGTGACTTGTTTGGTCAAGTTTGTGGTTATATCGATT
GCTCGGCTATTTCTGCCGATGGTAGCAAAGGTGAATATGGTGTTGCTTCC
TTCTGTTCTGATAAAGATCGTTTGTCATATGTGTTGAACCAGTATTACCT
TGACCAAGACAAGAAATCCAGTGCTTGTGATTTCAAAGGCAGTGCTTCAA
TCAATAGCAAGGCTAGTGCTAGTGGCAGCTGCAAAGCTGTTAGTGGAGTA
GCTACTGGTAAGGCATCTTCCTCTGGTGGAAGCTCCAAATCTGGATCTTC
CTCTGCATCTGCTTCTGGATCATCAAGCAGCAGCACCAGCTCTGGGTCCA
GCTCAAGCTCTGGAGTTAAAGCAACTCAACAAATGTCTATGGTCAAATTG
GTTTCAATTATTACTATTGTTACTGCATTTGTTGGTGGTATGTCCGTTGT
TTTTTAAATCAATGAAGACTAACCGATATGAAGGGTTCTGTTGTATAGGA
CGAATATATATAGTTTAATAAGAGTTCATTATTTAAAAGTTCCAATTTGA
AATCAACTTGGTACACATATCTATT

Design of Probes and Primers

Conventional probes that hybridize with the first selected nucleotide sequence of Table 1 were designed to provide a first oligonucleotide candidate group of 5961 probes. The probes were designed to satisfy the following criteria: (i) a $T_m$ value of 67° C. to 73° C.; (ii) a length of 15-35 nucleotides; (iii) exclusion of a mononucleotide $(G)_n$ run sequence in which n is at least 4.

23,015 tagging probes which hybridize with the first selected nucleotide sequence of Table 1 were designed. The tagging probes were designed in accordance with the second one of the design methods described above in such a manner that a non-hybridizable-non-complementary region to a 5'-tagging portion (12 mer) is selected and then a 3'-targeting portion is designed. The tagging probes were designed to satisfy the following criteria: (i) a $T_m$ value of 67° C. to 73° C.; (ii) a length of a targeting portion of 15-35 nucleotides; (iii) exclusion of a mononucleotide $(G)_n$ run sequence in which n is at least 4, (iv) a targeting portion of which 5'-end is G or C, (v) a targeting portion of which 5'-end portion (10 mer length) has GC content of 40% or more.

Primers (including forward primer and reverse primer) that hybridize with the first selected nucleotide sequence of Table 1 were designed to satisfy the following criteria, thereby providing 6,756 primers: (i) a $T_m$ value of 55° C. to 60° C.; (ii) a length of 18-25 nucleotides; (iii) exclusion of a mononucleotide $(G)_n$ run sequence in which n is at least 4.

Preparation of Reference Nucleotide Sequences

Reference nucleotide sequences with sequence similarity to the first selected nucleotide sequence of Table 1 were selected. The strains of *Candida albicans* carrying the selected reference nucleotide sequences were summarized in Table 2. In Table 2, tax_id is a number assigned from the GenBank Taxonomy DB.

The reference nucleotide sequences were selected to satisfy a sequence identity of 90% or more to the first selected nucleotide sequence. In addition to the selected sequences, nucleotide sequences as the reference nucleotide sequences were further selected to satisfy a sequence coverage value of 50% or more and (the sequence coverage value minus the sequence identity) of less than 5 for the first selected nucleotide sequence. Nucleotide sequences in which N (any nucleotide) is 5% or more were excluded from the selected sequences.

TABLE 2

| No | tax_Id | Strain name |
|---|---|---|
| 1 | 5476 | *Candida albicans* |
| 2 | 294748 | *Candida albicans* WO-1 |
| 3 | 294748 | *Candida albicans* WO-1 |
| 4 | 5476 | *Candida albicans* |
| 5 | 1182540 | *Candida albicans* A203 |
| 6 | 1182540 | *Candida albicans* A203 |
| 7 | 1094981 | *Candida albicans* 12C |
| 8 | 1094988 | *Candida albicans* GC75 |
| 9 | 1094998 | *Candida albicans* P76055 |
| 10 | 1094999 | *Candida albicans* P76067 |
| 11 | 1182531 | *Candida albicans* 3153A |
| 12 | 1182531 | *Candida albicans* 3153A |
| 13 | 1094990 | *Candida albicans* P57072 |
| 14 | 1094984 | *Candida albicans* P87 |
| 15 | 1094992 | *Candida albicans* P37037 |
| 16 | 1182533 | *Candida albicans* A20 |
| 17 | 1182533 | *Candida albicans* A20 |
| 18 | 237561 | *Candida albicans* SC5314 |
| 19 | 237561 | *Candida albicans* SC5314 |
| 20 | 237561 | *Candida albicans* SC5314 |
| 21 | 237561 | *Candida albicans* SC5314 |
| 22 | 1182534 | *Candida albicans* A48 |
| 23 | 1182534 | *Candida albicans* A48 |
| 24 | 1094993 | *Candida albicans* P37039 |
| 25 | 1094987 | *Candida albicans* 19F |
| 26 | 1182539 | *Candida albicans* A84 |
| 27 | 1182539 | *Candida albicans* A84 |
| 28 | 1094997 | *Candida albicans* P75063 |
| 29 | 1094989 | *Candida albicans* P78048 |
| 30 | 237561 | *Candida albicans* SC5314 |
| 31 | 1182536 | *Candida albicans* A92 |
| 32 | 1182536 | *Candida albicans* A92 |
| 33 | 1094986 | *Candida albicans* P60002 |
| 34 | 1165368 | *Candida albicans* Ca6 |

TABLE 2-continued

| No | tax_Id | Strain name |
|---|---|---|
| 35 | 237561 | *Candida albicans* SC5314 |
| 36 | 1094995 | *Candida albicans* P75016 |
| 37 | 1094982 | *Candida albicans* L26 |
| 38 | 1182538 | *Candida albicans* A155 |
| 39 | 1182538 | *Candida albicans* A155 |
| 40 | 1094985 | *Candida albicans* P37005 |
| 41 | 1094991 | *Candida albicans* P34048 |
| 42 | 1182537 | *Candida albicans* A123 |
| 43 | 1182537 | *Candida albicans* A123 |
| 44 | 1094996 | *Candida albicans* P57055 |
| 45 | 1182532 | *Candida albicans* CHN1 |
| 46 | 1182532 | *Candida albicans* CHN1 |
| 47 | 1095000 | *Candida albicans* P78042 |
| 48 | 5476 | *Candida albicans* |
| 49 | 1182535 | *Candida albicans* A67 |
| 50 | 1182535 | *Candida albicans* A67 |
| 51 | 1325634 | *Candida albicans* Ca529L |
| 52 | 1325634 | *Candida albicans* Ca529L |
| 53 | 1094983 | *Candida albicans* P94015 |
| 54 | 1094994 | *Candida albicans* P75010 |
| 55 | 237561 | *Candida albicans* SC5314 |
| 56 | 237561 | *Candida albicans* SC5314 |

Evaluation of a Target-Coverage and Introduction of a Degenerate Base

The target-coverage was evaluated by analyzing whether the first oligonucleotide candidate group comprising the designed probes and primers is matched to both the first selected nucleotide sequence of the target nucleic acid molecule and the reference nucleotide sequence. The first oligonucleotide candidate group comprises oligonucleotides (e.g., probes and primers) matched and mismatched to the first selected nucleotide sequence and the reference nucleotide sequence. Degenerate bases of no more than 3 were introduced into probes and primers showing a target-coverage of less than 100% for the first selected nucleotide sequence and the reference nucleotide sequence.

The probes and primers into which the degenerate bases were introduced were selected such that the target-coverages of the probes and primers increased to at least 70% by introduction of the degenerate bases. The number of the degenerate bases was permitted up to three as long as the target-coverages of the probes and primers increased up to 100%. The introduction of the degenerate bases was performed only when the target-coverage was increased. For example, where 50% target-coverage value of a probe is shown because 50% sequences among a total of reference nucleotide sequences have a deleted region where the probe is hybridized, degenerate bases do not need to introduce into the probe to increase its target-coverage. In Table 3, the first probe with a degenerate base has 96.4% target-coverage which does not further increase by additional introduction of degenerate bases, and therefore additional introduction of degenerate bases was not undertaken. Two sequences that are not covered by the first probe have four or more variations at a region where the probe hybridizes and three degenerate bases are introduced into the first probe not to reach to 100% target-coverage.

That is, the strategy for introduction of degenerate bases in Examples is to introduce degenerate bases within three bases such that a target-coverage becomes as high as 100%. When a target-coverage does not increase to 100% by introduction of degenerate bases of 3 or less, degenerate bases are introduced such that the highest target-coverage is obtained by introducing the least number of degenerate bases.

The modified oligonucleotides modified by introduction of the degenerate base were used together with the first oligonucleotide candidate group as a second oligonucleotide candidate group. Tables 3 and 4 show exemplary modified probes and modified primers generated by introduction of degenerate bases.

TABLE 3

| Probe sequence | Number of introduced degenerate bases | Actual use rate of probe patterns[1] | Probe pattern number[2] | Number of matched targets | Number of targets | Target coverage (%) |
|---|---|---|---|---|---|---|
| GYGTTGCAACATCAAAATCATTTC ATCGCTAAT (SEQ ID NO: 2) | 1 | 100 | 2 | 54 | 56 | 96.4 |
| CAAGTTGAYTTCAAATTGGAACTT TTAAATAATG (SEQ ID NO: 3) | 1 | 100 | 2 | 54 | 56 | 96.4 |
| GTTGAYTTCAAATTGGAACTTTTA AATAATGAWC (SEQ ID NO: 4) | 2 | 75 | 4 | 54 | 56 | 96.4 |
| CATACCAAACTACAGGTTGRAGSC AAAAAAAW (SEQ ID NO: 5) | 3 | 50 | 8 | 54 | 56 | 96.4 |
| CCAAACTACAGGTTGAAGSCAAAA AAAAWD (SEQ ID NO: 6) | 3 | 25 | 12 | 48 | 56 | 85.7 |
| GTATTCATTAATCAAATCATTGGY YACATTT (SEQ ID NO: 7) | 2 | 50 | 4 | 56 | 56 | 100 |
| GGYYACATTTGCCACACTCTTTTC ATTAA (SEQ ID NO: 8) | 2 | 50 | 4 | 56 | 56 | 100 |
| GYYACATTTGCCACACTCTTTTCA TTAACTTTA (SEQ ID NO: 9) | 2 | 50 | 4 | 56 | 56 | 100 |

[1] an actual use rate of probe patterns generated by introduction of the degenerate base;
[2] an probe pattern number generated by introduction of the degenerate base

TABLE 4

| Probe sequence | Number of introduced degenerate bases | Actual use rate of probe patterns[1] | Probe pattern number[2] | Number of matched targets | Number of targets | Target coverage (%) |
|---|---|---|---|---|---|---|
| TATAATAGGYGTTGCAACATCAAAA (SEQ ID NO: 10) | 1 | 100 | 2 | 54 | 56 | 96.4 |
| AGGYGTTGCAACATCAAAATCAT (SEQ ID NO: 11) | 1 | 100 | 2 | 54 | 56 | 96.4 |
| ACATACCAAACTACAGGTTGRAGS (SEQ ID NO: 12) | 2 | 75 | 4 | 54 | 56 | 96.4 |
| CAAACTACAGGTTGRAGSCAAA (SEQ ID NO: 13) | 2 | 75 | 4 | 54 | 56 | 96.4 |
| TACAGGTTGRAGSCAAAAAAAAW (SEQ ID NO: 14) | 3 | 50 | 8 | 54 | 56 | 85.7 |
| CAGGTTGAAGSCAAAAAAAAWD (SEQ ID NO: 15) | 3 | 25 | 12 | 48 | 56 | 100 |
| CATTAATCAAATCATTGGYYA (SEQ ID NO: 16) | 2 | 50 | 4 | 56 | 56 | 100 |
| CKTCCACYCCACCARTTG (SEQ ID NO: 17) | 3 | 37.5 | 8 | 56 | 56 | 100 |

[1] an actual use rate of probe patterns generated by introduction of the degenerate base;
[2] an probe pattern number generated by introduction of the degenerate base Preparation of a Third Oligonucleotide Candidate Group A third oligonucleotide candidate group was prepared by selection from the second oligonucleotide candidate group (probes, tagging probes and primers). Two selection steps were carried out.

(1) Acquisition of an Above-Average Candidate Group Based on Selection Criteria

First, in the second oligonucleotide candidate group, oligonucleotides in the upper 50% were selected for each of the following selection criteria: (i) the number of degenerate bases used (ascending order); (ii) an actual use rate of oligonucleotide patterns generated by introduction of degenerate bases (descending order); (iii) an oligonucleotide pattern number generated by introduction of the degenerate base (ascending order); (iv) a target-coverage for both a target nucleic acid molecule and at least one reference nucleic acid molecule (descending order); (v) for tagging probes, the non-complementarity level of the first tagging part (descending order); (vi) when an oligonucleotide forms a homodimer, the number or proportion of consecutive nucleotides involved in the formation of the homodimer (continuous dimer maximum value) (ascending order); and (vii) a hairpin structure-forming free energy value (ΔG value) (descending order).

An oligonucleotide having a degenerate base(s) actually includes a plurality of oligonucleotides. When evaluating such a degenerate oligonucleotide with regard to the selection criterion (vi), an oligonucleotide with the largest number or proportion of consecutive nucleotides involved in the formation of a homodimer is evaluated among a plurality of oligonucleotides represented by the degenerate oligonucleotide. When evaluating such a degenerate oligonucleotide with regard to the selection criterion (vii), an oligonucleotide with the smallest ΔG value is evaluated among a plurality of oligonucleotides represented by the degenerate oligonucleotide.

(2) Sorting of Candidate Group According to Selection Ranks

Afterwards, the acquired candidate group in the upper 50% was assigned selection ranks in accordance with each of the following priority items: (i) a target-coverage for both the first selected nucleotide sequence and at least one reference nucleotide sequence; wherein the higher the target-coverage, the higher the priority, (ii) an actual use rate of oligonucleotide patterns generated by introduction of degenerate bases; wherein the higher the actual use ratio, the higher the priority, (iii) the number or proportion of the degenerate base or the universal base used; wherein the smaller the number or proportion, the higher the priority, (iv) when the oligonucleotide forms a homodimer, the number or proportion of consecutive nucleotides involved in the formation of the homodimer; wherein the smaller the number or proportion, the higher the priority, (v) a hairpin structure-forming free energy value (ΔG value); wherein the higher the free energy value, the higher the priority, (vi) a length; wherein the shorter the length, the higher the priority, (vii) for the tagging probe, the non-complementarity level of the first tagging part; wherein the higher the non-complementarity level, the higher the priority.

The seven priority items differ from each other in terms of criticality, the priority item (i) has the highest criticality, and then the criticality is assigned from the priority item (ii) to item (vii) in order. By ranking for the priority item (i) with the highest criticality, a top-most oligonucleotide was selected as an actual use oligonucleotide for the detection of the target nucleic acid sequence. When a plurality of top-most oligonucleotides were present in the priority item (i), ranks for the priority item with just lower criticality than the highest criticality (i.e., the priority item (ii)) were compared to find a top-most oligonucleotide as an actual use oligonucleotide.

After a top-most probe was selected from the prioritized probes, and a primer suitable for the top-most probe was selected from the third oligonucleotide candidate group. The suitable primer was selected from primers which form an amplicon having a suitable size (200-500 nucleotides) and do not form a heterodimer with the selected probe. Where a primer suitable for the top-most probe was absent in the third oligonucleotide candidate group, a primer was re-selected for a probe with just lower rank than the top-most probe. A combination of the re-selected primer and the probe with just lower rank than the top-most probe was determined as actual use oligonucleotides.

Table 5 shows exemplary actual use oligonucleotides (five combinations of tagging probes and primers) finally selected in accordance with the present invention for detecting target nucleic acid molecules in a sample.

(strains of Nos. 1, 2, 5, 7 or 11 in Table 2), 10 pmole of upstream primer (SEQ ID NO:24), 10 pmole of downstream primer (SEQ ID NO:25), 5 pmole of the tagging oligonucleotide (SEQ ID NOs:18 and 19) as the PTO, 2 pmole of the CTO (TTTTCTTTTCTTTTCTTTTC[T(FAM)]TTTTGTATCGTCGGGAC; SEQ ID NO:34), 10 µl of 2× Master Mix containing 2.5 mM MgCl$_2$, 200 µM of dNTPs and 1.6 units of H-Taq DNA polymerase (Solgent, Korea); a tube containing the reaction mixture was placed on the real-time thermocycler (CFX96, Bio-Rad); the reaction mixture was denatured for 15 min at 95° C. and subjected to 60 cycles of 30 sec at 95° C., 60 sec at 60° C. and 30 sec at 72° C. Signals at 60° C. of each cycle were detected to determine the presence or absence of *Candida albicans*.

The reaction results according to the PTOCE method showed that target signals (around $C_t$ 30-33) were successfully detected in the presence of the target nucleic acid sequence, demonstrating that the tagging probe and primers prepared in Example works well as probe and primers (FIGS. 2 to 6). FIGS. 2 to 6 are amplification curves of strains of Nos. 1, 2, 5, 7 or 11 in Table 2, respectively. No signal was detected in the absence of the template.

TABLE 5

| Sequence of tagging portion of top-most probe | Sequence of targeting portion of top-most probe | Sequence of suitable primers |
|---|---|---|
| GTCCCGACGATA (SEQ ID NO: 18) | CATTGCCGATTATTTCTCTTGTGGTTCA (SEQ ID NO: 19) | TTGGGATTTTTTGCTGGTAA (SEQ ID NO: 24) AGTTGATTTGCCACACCATTC (SEQ ID NO: 25) |
| | GATAAATCAGCAACAATGTAAATACCAGCG (SEQ ID NO: 20) | TGAGAGTTTATGCTATTGACCCA (SEQ ID NO: 26) CCAGCAAAAAATCCCAAAAC (SEQ ID NO: 27) |
| | GTATGAATGGTGTGGCAAATCAACTTTCG (SEQ ID NO: 21) | GCCATTGCCGATTATTTCTC (SEQ ID NO: 28) TCGGAGAAGAAGGCTGGG (SEQ ID NO: 29) |
| | GACGCTGGTATTTACATTGTTGCTGATTT (SEQ ID NO: 22) | TGAGAGTTTATGCTATTGACCCA (SEQ ID NO: 30) CCAGCAAAAAATCCCAAAAC (SEQ ID NO: 31) |
| | GTTACCAGCAAAAAATCCCAAAACATTAG (SEQ ID NO: 23) | CAGAAACAACCCAGAATGGAA (SEQ ID NO: 32) GAGAAATAATCGGCAATGGC (SEQ ID NO: 33) |

Example 2

Detection of *Candida albicans*

The oligonucleotides finally prepared (the 5'-tagging probe comprising the 5'-tagging portion of SEQ ID NO:18 and the 3'-targeting portion of SEQ ID NO:19, and the primer set of SEQ ID NOs:24 and 25 in Table 5) were analyzed whether they can serve as tagging probes or primers for detection of *Candida albicans* in the PTOCE method (see WO 2012/096523) involving target amplification and cleavage of probe (5'-tagging probe).

The reactions for the PTOCE method were conducted in the final volume of 20 µl containing 2 pmol of templates Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for preparing oligonucleotides for detecting a target nucleic acid molecule in a sample, comprising:
    designing oligonucleotides for detecting the target nucleic acid molecule in the sample using a first selected nucleotide sequence of the target nucleic acid molecule comprised in information related to the target nucleic acid molecule to provide a first oligonucleotide candidate group; wherein the first oligonucleotide candidate group comprises a probe and/or a primer comprising a nucleotide sequence complementary to the first selected nucleotide sequence of the target nucleic acid molecule;
    providing at least one reference nucleotide sequence with sequence similarity to the first selected nucleotide sequence of the target nucleic acid molecule;
    providing a second oligonucleotide candidate group using the first oligonucleotide candidate group; wherein the provision is performed by at least one of the followings;
        (a-1) in the first oligonucleotide candidate group, selecting at least one oligonucleotide showing a predetermined target-coverage for the first selected nucleotide sequence and the at least one reference nucleotide sequence to provide a second oligonucleotide candidate group comprising the at least one oligonucleotide; and
        (a-2) in the first oligonucleotide candidate group, replacing with a degenerate base and/or a universal base at least one base of at least one oligonucleotide showing a target-coverage of less than 100% for the first selected nucleotide sequence and at least one reference nucleotide sequence to provide a modified oligonucleotide with increased target-coverage, thereby providing the second oligonucleotide candidate group comprising the modified oligonucleotide; and
    selecting oligonucleotide(s) depending on a predetermined selection criterion from the second oligonucleotide candidate group to provide a third oligonucleotide candidate group; wherein the third oligonucleotide candidate group is used for detecting the target nucleic acid molecule in the sample.

2. The method according to claim 1, wherein the target nucleic acid molecule is a nucleic acid molecule that exhibits genetic diversity.

3. The method according to claim 1, wherein the information related to the target nucleic acid molecule further comprises at least one information selected from the group consisting of a name of a target organism from which the target nucleic acid molecule is derived, a taxonomy of a target organism, a name of the target nucleic acid molecule and an identifier of the target nucleic acid molecule in a public accessible sequence database.

4. The method according to claim 1, wherein the probe is a tagging probe comprising a targeting portion comprising a hybridizable-complementary nucleotide sequence to the first selected nucleotide sequence of the target nucleic acid molecule and a tagging portion comprising a non-hybridizable-non-complementary nucleotide sequence to the first selected nucleotide sequence of the target nucleic acid molecule.

5. The method according to claim 4, wherein the tagging probe is provided by a method comprising the following steps:
    (a) selecting the hybridizable-complementary nucleotide sequence to the first selected nucleotide sequence of the target nucleic acid molecule for the targeting portion and the non-hybridizable-non-complementary nucleotide sequence to the first selected nucleotide sequence of the target nucleic acid molecule for the tagging portion; wherein the tagging portion comprises a first tagging part of 3-8 nucleotides in length adjacent to the targeting portion and a second tagging part of 4-40 nucleotides in length adjacent to the first tagging part; the non-hybridizable-non-complementary nucleotide sequence for the tagging portion is selected not to be hybridized with the first selected nucleotide sequence of the target nucleic acid molecule; wherein a non-hybridizable-non-complementary nucleotide sequence of the first tagging part is selected by an independent non-complementarity level such that a sequence with a non-complementarity level satisfying a predetermined threshold value criterion is selected as the non-hybridizable-non-complementary nucleotide sequence of the first tagging part; and
    (b) preparing the tagging probe comprising (i) the targeting portion comprising the selected hybridizable-complementary nucleotide sequence and (ii) the tagging portion comprising the selected non-hybridizable-non-complementary nucleotide sequence.

6. The method according to claim 4, wherein the tagging probe is provided by a method comprising the following steps:
    (a) providing a nucleotide sequence for the tagging portion; wherein the tagging portion comprises a first tagging part adjacent to the targeting portion and a second tagging part adjacent to the first tagging part;
    (b) selecting in the first selected nucleotide sequence of the target nucleic acid molecule one or more non-hybridizable-non-complementary regions to the nucleotide sequence for the tagging portion by (i) selecting at least one region in the first selected nucleotide sequence of the target nucleic acid molecule and (ii) evaluating a non-complementarity level of the selected at least one region to the nucleotide sequence for the tagging portion;
    (c) selecting a nucleotide sequence for the targeting portion by (i) selecting a nucleotide sequence with a predetermined length in the first selected nucleotide sequence of the target nucleic acid molecule that is adjacent to the non-hybridizable-non-complementary region to the nucleotide sequence of the tagging portion and (ii) selecting a hybridizable-complementary nucleotide sequence to the selected nucleotide sequence in the first selected nucleotide sequence of the target nucleic acid molecule as the nucleotide sequence for the targeting portion; and (d) preparing the tagging probe comprising the nucleotide sequence of the tagging portion provided in the step (a) and the nucleotide sequence of the targeting portion selected in the step (c).

7. The method according to claim 1, wherein the designed first oligonucleotide candidate group comprises a probe designed to satisfy at least one of the following criteria:
  (i) a Tm value of 50° C. to 85° C.;
  (ii) a length of 15-50 nucleotides;
  (iii) exclusion of a mononucleotide (G)n run sequence in which n is at least 3;
  (iv) GC content of the 5'-end portion of 40% or more;
  (v) for the tagging probe, the targeting portion of which 5'-end is G or C; and
  (vi) for the tagging probe, the targeting portion of which 5'-end portion has GC content of 40% or more.

8. The method according to claim 1, wherein the designed first oligonucleotide candidate group comprises a primer designed to satisfy at least one of the following criteria:
  (i) a Tm value of 40° C. to 70° C.;
  (ii) a length of 15-50 nucleotides; and
  (iii) exclusion of a mononucleotide (G)n run sequence in which n is at least 3.

9. The method according to claim 1, wherein the at least one reference nucleotide sequence showing sequence similarity to the first selected nucleotide sequence of the target nucleic acid molecule is a nucleic acid molecule having the same gene name as the target nucleic acid molecule.

10. The method according to claim 1, wherein the at least one reference nucleotide sequence showing sequence similarity is a nucleotide sequence satisfying the following criterion:
  a sequence identity of 70% or more to the first selected nucleotide sequence of the target nucleic acid molecule.

11. The method according to claim 1, wherein the method further comprises, before providing the second oligonucleotide candidate group, evaluating a target-coverage of the first oligonucleotide candidate group by analyzing whether the first oligonucleotide candidate group is hybridized with the first selected nucleotide sequence and at least one reference nucleotide sequence.

12. The method according to claim 1, wherein the modified oligonucleotide with increased target-coverage in the step (a-2) are oligonucleotides prepared in such a manner that at least one base of each of all oligonucleotides in the first oligonucleotide candidate group whose target-coverage is enabled to be increased by introduction of the degenerate base and/or the universal base is replaced with the degenerate base and/or the universal base.

13. The method according to claim 1, wherein the modified oligonucleotide with increased target-coverage in the step (a-2) are oligonucleotides prepared in such a manner that at least one base of each of all oligonucleotides in the first oligonucleotide candidate group whose target-coverage is enabled to show a predetermined target-coverage by the introduction of the degenerate base and/or the universal base is replaced with the degenerative base and/or the universal base.

14. The method according to claim 1, wherein the modified oligonucleotide with increased target-coverage in the step (a-2) are oligonucleotides prepared in such a manner that modified oligonucleotides having the highest target-coverage by introducing the least number of the degenerate base and/or the universal base are selected among modified oligonucleotides provided by introducing the degenerate base and/or the universal base of no more than a predetermined number into at least two oligonucleotides of the first oligonucleotide candidate group.

15. The method according to claim 1, wherein the number of bases replaced with the degenerate base and/or the universal base in the step (a-2) is 25% or less based on a total length of a portion hybridized with the target nucleic acid molecule in the oligonucleotide.

16. The method according to claim 1, wherein the second oligonucleotide candidate group provided by the step (a-2) further comprises at least one of the followings: (i) an oligonucleotide showing the target coverage of 100% and (ii) an oligonucleotide whose target-coverage falls within the predetermined target-coverage and is not increased by replacing with the degenerate base and/or the universal bases.

17. The method according to claim 1, wherein the predetermined selection criterion for selecting the oligonucleotide from the second oligonucleotide candidate group to provide the third oligonucleotide candidate group is at least one criterion selected from the group consisting of: (i) the number or proportion of the degenerate base and/or the universal base used; (ii) an actual use rate of oligonucleotide patterns generated by introduction of the degenerate base; (iii) an oligonucleotide pattern number generated by introduction of the degenerate base; (iv) the target-coverage for the first selected nucleotide sequence of the target nucleic acid molecule and at least one reference nucleotide sequence; (v) for the tagging probe the non-complementarity level of the first tagging part; (vi) when the oligonucleotide forms a homodimer, the number or proportion of consecutive nucleotides involved in the formation of the homodimer; (vii) a hairpin structure-forming free energy value (ΔG value); (viii) a Tm value; (ix) a GC content; and (x) a length.

18. The method according to claim 1, wherein the method further comprises assigning ranks to the oligonucleotides of the third oligonucleotide candidate group in accordance with at least one of the following priority items:
  (i) the target-coverage for the first selected nucleotide sequence of the target nucleic acid molecule and at least one reference nucleotide sequence; wherein the higher the target-coverage, the higher the priority,
  (ii) an actual use rate of oligonucleotide patterns generated by introduction of the degenerate base; wherein the higher the actual use ratio, the higher the priority,
  (iii) the number or proportion of the degenerate base and/or the universal base used; wherein the smaller the number or proportion of the degenerate base and/or the universal base, the higher the priority,
  (iv) when the oligonucleotide forms a homodimer, the number or proportion of consecutive nucleotides involved in the formation of the homodimer; wherein the smaller the number or proportion, the higher the priority,
  (v) a hairpin structure-forming free energy value (ΔG value); wherein the higher the free energy value, the higher the priority, (vi) a length; wherein the shorter the length, the higher the priority, (vii) for the tagging probe of the non-complementarity level of the first tagging part;

wherein the higher the non-complementarity level, the higher the priority.

19. A computer readable storage medium containing instructions to configure a processor to perform a method for preparing oligonucleotides for detecting a target nucleic acid molecule in a sample, the method comprising:

designing oligonucleotides for detecting the target nucleic acid molecule in the sample using a first selected nucleotide sequence of the target nucleic acid molecule comprised in information related to the target nucleic acid molecule to provide a first oligonucleotide candidate group; wherein the first oligonucleotide candidate group comprises a probe and/or a primer comprising a nucleotide sequence complementary to the first selected nucleotide sequence of the target nucleic acid molecule;

providing at least one reference nucleotide sequence with sequence similarity to the first selected nucleotide sequence of the target nucleic acid molecule;

providing a second oligonucleotide candidate group using the first oligonucleotide candidate group; wherein the provision is performed by at least one of the followings;

(a-1) in the first oligonucleotide candidate group, selecting at least one oligonucleotide showing a predetermined target-coverage for the first selected nucleotide sequence and the at least one reference nucleotide sequence is selected to provide a second oligonucleotide candidate group comprising the at least one oligonucleotide; and (a-2) in the first oligonucleotide candidate group, replacing with a degenerate base and/or a universal base at least one base of at least one oligonucleotide showing a target-coverage of less than 100% for the first selected nucleotide sequence and at least one reference nucleotide sequence to provide a modified oligonucleotide with increased target-coverage, thereby providing the second oligonucleotide candidate group comprising the modified oligonucleotide; and selecting oligonucleotide(s) depending on a predetermined selection criterion from the second oligonucleotide candidate group to provide a third oligonucleotide candidate group; wherein the third oligonucleotide candidate group is used for detecting the target nucleic acid molecule in the sample.

\* \* \* \* \*

SEQUENCE LISTING

<160> NUMBER OF SEQ ID NOS: 34

<210> SEQ ID NO 1
<211> LENGTH: 2026
<212> TYPE: DNA
<213> ORGANISM: Candida albicans
<220> FEATURE:
<221> NAME/KEY: gene
<222> LOCATION: (1)..(2026)
<223> OTHER INFORMATION: PHR1 gene sequence

<400> SEQUENCE: 1

| | | | | | |
|---|---|---|---|---|---|
| gaattcatcg | acgcctcatt | catactaata | taataggtgt | tgcaacatca | aaatcatttc | 60 |
| atcgctaata | caaacatccg | agattaatct | tgtccattgg | caatataatt | aacaccactg | 120 |
| ccaatacata | taaatcaaat | cagcattaac | taatagtatt | tattaattac | ttagaaaagc | 180 |
| cgggctgcgt | ttttttgttt | cattcataga | tttacttatt | tccatttaac | ataccaaact | 240 |
| acaggttgaa | gccaaaaaaa | aatgtattca | ttaatcaaat | cattggccac | atttgccaca | 300 |
| ctcttttcat | taactttagc | caagtttgaa | tcgtccaccc | caccagttga | agttgttggt | 360 |
| aacaaatttt | attttttccaa | taatgggtct | cagttttttaa | tcaggggtat | cgcctatcag | 420 |
| caagatgccg | cgggctcagt | ttcctccggt | tacgacgccg | atcctaatag | aaaatacaat | 480 |
| gatcctttag | ccgatcgtga | cgcttgtaaa | cgtgacgtca | agtatttcaa | agaatcaaac | 540 |
| accaatactt | tgagagttta | tgctattgac | ccagataagg | atcatgaaga | gtgtatgaaa | 600 |
| attttcagtg | acgctggtat | ttacattgtt | gctgatttat | cagaaccaac | tgtatcgatt | 660 |
| aacagaaaca | acccagaatg | gaacttggat | ttatacaaac | gttatacaaa | agtcattgat | 720 |
| aagatgcaag | aatattctaa | tgttttggga | ttttttgctg | gtaacgaagt | aactaataat | 780 |
| cgttcaaata | ccgatgcttc | tgcatttgtt | aaggctgcca | ttagagatat | gaagaaatac | 840 |
| atcaaggagt | ctgattatag | acaaattcct | gttggttatt | catccaatga | tgacgaagaa | 900 |
| attagagtcg | ccattgccga | ttatttctct | tgtggttcat | tagatgatcg | tgctgatttc | 960 |
| tttggtatca | atatgtatga | atggtgtggc | aaatcaactt | tcgaaacctc | aggttacaag | 1020 |
| gacagaactg | aagaaatcaa | gaacttgact | atcccagcct | tcttctccga | atatggatgt | 1080 |
| aatgctaacc | gtccacgttt | gttccaagaa | attggtacct | tgtattccga | taagatgact | 1140 |
| gatgtttggt | ccggaggtat | tgtttatatg | tattttgaag | aggctaacaa | atacggtttg | 1200 |
| gttctggttg | atggtaattc | ggtcaagaca | ttatctgact | acaacaatta | caaatcagaa | 1260 |
| atgaacaaaa | taagcccatc | ccttgcccat | acttcaacat | tatccagttc | tgacgccagc | 1320 |
| aagactttgc | aatgtccagg | aactgctgct | agcacttgga | aagctgcaac | taatttgcca | 1380 |
| ccaactccag | atgaaagtta | ctgtgattgt | atttccaagt | cattagaatg | tgttgttgct | 1440 |
| gacgatgttg | ataaagaaga | ctatggtgac | ttgtttggtc | aagtttgtgg | ttatatcgat | 1500 |
| tgctcggcta | tttctgccga | tggtagcaaa | ggtgaatatg | tgttgcttc | cttctgttct | 1560 |
| gataaagatc | gtttgtcata | tgtgttgaac | cagtattacc | ttgaccaaga | caagaaatcc | 1620 |
| agtgcttgtg | atttcaaagg | cagtgcttca | atcaatagca | aggctagtgc | tagtggcagc | 1680 |
| tgcaaagctg | ttagtggagt | agctactggt | aaggcatctt | cctctggtgg | aagctccaaa | 1740 |
| tctgatctct | cctctgcatc | tgcttctgga | tcatcaagca | gcagcaccag | ctctgggtcc | 1800 |
| agctcaagct | ctggagttaa | agcaactcaa | caaatgtcta | tggtcaaatt | ggtttcaatt | 1860 |
| attactattg | ttactgcatt | tgttggtggt | atgtccgttg | ttttttaaat | caatgaagac | 1920 |
| taaccgatat | gaagggttct | gttgtatagg | acgaatatat | atagtttaat | aagagttcat | 1980 | tatttaaaag ttccaatttg aaatcaactt ggtacacata tctatt 2026

<210> SEQ ID NO 2
<211> LENGTH: 33
<212> TYPE: DNA
<213> ORGANISM: Artificial Sequence
<220> FEATURE:
<223> OTHER INFORMATION: Synthetic nucleotide: Probe sequence

<400> SEQUENCE: 2
gygttgcaac atcaaaatca tttcatcgct aat 33

<210> SEQ ID NO 3
<211> LENGTH: 34
<212> TYPE: DNA
<213> ORGANISM: Artificial Sequence
<220> FEATURE:
<223> OTHER INFORMATION: Synthetic nucleotide: Probe sequence

<400> SEQUENCE: 3
caagttgayt tcaaattgga acttttaaat aatg 34

<210> SEQ ID NO 4
<211> LENGTH: 34
<212> TYPE: DNA
<213> ORGANISM: Artificial Sequence
<220> FEATURE:
<223> OTHER INFORMATION: Synthetic nucleotide: Probe sequence

<400> SEQUENCE: 4
gttgayttca aattggaact tttaaataat gawc 34

<210> SEQ ID NO 5
<211> LENGTH: 33
<212> TYPE: DNA
<213> ORGANISM: Artificial Sequence
<220> FEATURE:
<223> OTHER INFORMATION: Synthetic nucleotide: Probe sequence

<400> SEQUENCE: 5
cataccaaac tacaggttgr agscaaaaaa aaw 33

<210> SEQ ID NO 6
<211> LENGTH: 30
<212> TYPE: DNA
<213> ORGANISM: Artificial Sequence
<220> FEATURE:
<223> OTHER INFORMATION: Synthetic nucleotide: Probe sequence

<400> SEQUENCE: 6
ccaaactaca ggttgaagsc aaaaaaaawd 30

<210> SEQ ID NO 7
<211> LENGTH: 31
<212> TYPE: DNA
<213> ORGANISM: Artificial Sequence
<220> FEATURE:
<223> OTHER INFORMATION: Synthetic nucleotide: Probe sequence

<400> SEQUENCE: 7
gtattcatta atcaaatcat tggyyacatt t 31

<210> SEQ ID NO 8
<211> LENGTH: 29
<212> TYPE: DNA

```
<213> ORGANISM: Artificial Sequence
<220> FEATURE:
<223> OTHER INFORMATION: Synthetic nucleotide: Probe sequence

<400> SEQUENCE: 8
ggyyacattt gccacactct tttcattaa                                29

<210> SEQ ID NO 9
<211> LENGTH: 33
<212> TYPE: DNA
<213> ORGANISM: Artificial Sequence
<220> FEATURE:
<223> OTHER INFORMATION: Synthetic nucleotide: Probe sequence

<400> SEQUENCE: 9
gyyacatttg ccacactctt ttcattaact tta                           33

<210> SEQ ID NO 10
<211> LENGTH: 25
<212> TYPE: DNA
<213> ORGANISM: Artificial Sequence
<220> FEATURE:
<223> OTHER INFORMATION: Synthetic nucleotide: Primer sequence

<400> SEQUENCE: 10
tataataggy gttgcaacat caaaa                                    25

<210> SEQ ID NO 11
<211> LENGTH: 23
<212> TYPE: DNA
<213> ORGANISM: Artificial Sequence
<220> FEATURE:
<223> OTHER INFORMATION: Synthetic nucleotide: Primer sequence

<400> SEQUENCE: 11
aggygttgca acatcaaaat cat                                      23

<210> SEQ ID NO 12
<211> LENGTH: 24
<212> TYPE: DNA
<213> ORGANISM: Artificial Sequence
<220> FEATURE:
<223> OTHER INFORMATION: Synthetic nucleotide: Primer sequence

<400> SEQUENCE: 12
acataccaaa ctacaggttg rags                                     24

<210> SEQ ID NO 13
<211> LENGTH: 22
<212> TYPE: DNA
<213> ORGANISM: Artificial Sequence
<220> FEATURE:
<223> OTHER INFORMATION: Synthetic nucleotide: Primer sequence

<400> SEQUENCE: 13
caaactacag gttgragsca aa                                       22

<210> SEQ ID NO 14
<211> LENGTH: 23
<212> TYPE: DNA
<213> ORGANISM: Artificial Sequence
<220> FEATURE:
<223> OTHER INFORMATION: Synthetic nucleotide: Primer sequence

<400> SEQUENCE: 14
tacaggttgr agscaaaaaa aaw                                      23
```

<210> SEQ ID NO 15
<211> LENGTH: 22
<212> TYPE: DNA
<213> ORGANISM: Artificial Sequence
<220> FEATURE:
<223> OTHER INFORMATION: Synthetic nucleotide: Primer sequence

<400> SEQUENCE: 15
caggttgaag scaaaaaaaa wd                                           22

<210> SEQ ID NO 16
<211> LENGTH: 21
<212> TYPE: DNA
<213> ORGANISM: Artificial Sequence
<220> FEATURE:
<223> OTHER INFORMATION: Synthetic nucleotide: Primer sequence

<400> SEQUENCE: 16
cattaatcaa atcattggyy a                                            21

<210> SEQ ID NO 17
<211> LENGTH: 18
<212> TYPE: DNA
<213> ORGANISM: Artificial Sequence
<220> FEATURE:
<223> OTHER INFORMATION: Synthetic nucleotide: Primer sequence

<400> SEQUENCE: 17
cktccacycc accarttg                                                18

<210> SEQ ID NO 18
<211> LENGTH: 12
<212> TYPE: DNA
<213> ORGANISM: Artificial Sequence
<220> FEATURE:
<223> OTHER INFORMATION: Synthetic nucleotide: Sequence of tagging
      portion

<400> SEQUENCE: 18
gtcccgacga ta                                                      12

<210> SEQ ID NO 19
<211> LENGTH: 28
<212> TYPE: DNA
<213> ORGANISM: Artificial Sequence
<220> FEATURE:
<223> OTHER INFORMATION: Synthetic nucleotide: Sequence of targeting
      portion

<400> SEQUENCE: 19
cattgccgat tatttctctt gtggttca                                     28

<210> SEQ ID NO 20
<211> LENGTH: 30
<212> TYPE: DNA
<213> ORGANISM: Artificial Sequence
<220> FEATURE:
<223> OTHER INFORMATION: Synthetic nucleotide: Sequence of targeting
      portion

<400> SEQUENCE: 20
gataaatcag caacaatgta aataccagcg                                   30

<210> SEQ ID NO 21
<211> LENGTH: 29

```
<212> TYPE: DNA
<213> ORGANISM: Artificial Sequence
<220> FEATURE:
<223> OTHER INFORMATION: Synthetic nucleotide: Sequence of targeting
      portion

<400> SEQUENCE: 21
gtatgaatgg tgtggcaaat caactttcg                                      29

<210> SEQ ID NO 22
<211> LENGTH: 29
<212> TYPE: DNA
<213> ORGANISM: Artificial Sequence
<220> FEATURE:
<223> OTHER INFORMATION: Synthetic nucleotide: Sequence of targeting
      portion

<400> SEQUENCE: 22
gacgctggta tttacattgt tgctgattt                                      29

<210> SEQ ID NO 23
<211> LENGTH: 29
<212> TYPE: DNA
<213> ORGANISM: Artificial Sequence
<220> FEATURE:
<223> OTHER INFORMATION: Synthetic nucleotide: Sequence of targeting
      portion

<400> SEQUENCE: 23
gttaccagca aaaatccca aaacattag                                       29

<210> SEQ ID NO 24
<211> LENGTH: 20
<212> TYPE: DNA
<213> ORGANISM: Artificial Sequence
<220> FEATURE:
<223> OTHER INFORMATION: Synthetic nucleotide: Primer sequence

<400> SEQUENCE: 24
ttgggatttt ttgctggtaa                                                20

<210> SEQ ID NO 25
<211> LENGTH: 21
<212> TYPE: DNA
<213> ORGANISM: Artificial Sequence
<220> FEATURE:
<223> OTHER INFORMATION: Synthetic nucleotide: Primer sequence

<400> SEQUENCE: 25
agttgatttg ccacaccatt c                                              21

<210> SEQ ID NO 26
<211> LENGTH: 23
<212> TYPE: DNA
<213> ORGANISM: Artificial Sequence
<220> FEATURE:
<223> OTHER INFORMATION: Synthetic nucleotide: Primer sequence

<400> SEQUENCE: 26
tgagagttta tgctattgac cca                                            23

<210> SEQ ID NO 27
<211> LENGTH: 20
<212> TYPE: DNA
<213> ORGANISM: Artificial Sequence
<220> FEATURE:
<223> OTHER INFORMATION: Synthetic nucleotide:  Primer sequence
```

```
<400> SEQUENCE: 27
ccagcaaaaa atcccaaaac                                                      20

<210> SEQ ID NO 28
<211> LENGTH: 20
<212> TYPE: DNA
<213> ORGANISM: Artificial Sequence
<220> FEATURE:
<223> OTHER INFORMATION: Synthetic nucleotide: Primer sequence

<400> SEQUENCE: 28
gccattgccg attatttctc                                                      20

<210> SEQ ID NO 29
<211> LENGTH: 18
<212> TYPE: DNA
<213> ORGANISM: Artificial Sequence
<220> FEATURE:
<223> OTHER INFORMATION: Synthetic nucleotide: Primer sequence

<400> SEQUENCE: 29
tcggagaaga aggctggg                                                        18

<210> SEQ ID NO 30
<211> LENGTH: 23
<212> TYPE: DNA
<213> ORGANISM: Artificial Sequence
<220> FEATURE:
<223> OTHER INFORMATION: Synthetic nucleotide: Primer sequence

<400> SEQUENCE: 30
tgagagttta tgctattgac cca                                                  23

<210> SEQ ID NO 31
<211> LENGTH: 20
<212> TYPE: DNA
<213> ORGANISM: Artificial Sequence
<220> FEATURE:
<223> OTHER INFORMATION: Synthetic nucleotide: Primer sequence

<400> SEQUENCE: 31
ccagcaaaaa atcccaaaac                                                      20

<210> SEQ ID NO 32
<211> LENGTH: 21
<212> TYPE: DNA
<213> ORGANISM: Artificial Sequence
<220> FEATURE:
<223> OTHER INFORMATION: Synthetic nucleotide: Primer sequence

<400> SEQUENCE: 32
cagaaacaac ccagaatgga a                                                    21

<210> SEQ ID NO 33
<211> LENGTH: 20
<212> TYPE: DNA
<213> ORGANISM: Artificial Sequence
<220> FEATURE:
<223> OTHER INFORMATION: Synthetic nucleotide: Primer sequence

<400> SEQUENCE: 33
gagaaataat cggcaatggc                                                      20

<210> SEQ ID NO 34
```

```
<211> LENGTH: 38
<212> TYPE: DNA
<213> ORGANISM: Artificial Sequence
<220> FEATURE:
<223> OTHER INFORMATION: Synthetic nucleotide: CTO sequence

<400> SEQUENCE: 34
ttttcttttc ttttcttttc tttttgtatc gtcgggac                              38
```